(12) United States Patent
Boenitz-Dulat et al.

(10) Patent No.: US 10,968,469 B2
(45) Date of Patent: Apr. 6, 2021

(54) PROLINE HYDROXYLASES AS WELL AS USES, METHODS AND PRODUCTS INVOLVING THE SAME

(71) Applicant: Hoffmann-La Roche Inc., Little Falls, NJ (US)

(72) Inventors: Mara Boenitz-Dulat, Penzberg (DE); Hans Iding, Basel (CH); Dennis Wetzl, Basel (CH); Alessa Hinzmann, Basel (CH)

(73) Assignee: F. Hoffmann-La Roche, Inc., Little Falls, NJ (US)

( * ) Notice: Subject to any disclaimer, the term of this patent is extended or adjusted under 35 U.S.C. 154(b) by 101 days.

(21) Appl. No.: 16/197,430

(22) Filed: Nov. 21, 2018

(65) Prior Publication Data
US 2019/0153491 A1 May 23, 2019

(30) Foreign Application Priority Data
Nov. 23, 2017 (EP) ..................... 17001927

(51) Int. Cl.
*C12P 17/12* (2006.01)
*C12N 9/14* (2006.01)
*C12N 9/02* (2006.01)

(52) U.S. Cl.
CPC ............ *C12P 17/12* (2013.01); *C12N 9/0071* (2013.01); *C12N 9/14* (2013.01)

(58) Field of Classification Search
CPC .......... C12P 17/12; C12N 9/0071; C12N 9/14
See application file for complete search history.

(56) References Cited

FOREIGN PATENT DOCUMENTS

| CN | 106834244 A | 6/2017 |
|---|---|---|
| WO | 2017/057730 A1 | 4/2017 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Varghese, N., GenBank accession No. SCF23490, Aug. 15, 2016.*

* cited by examiner

*Primary Examiner* — Delia M Ramirez
(74) *Attorney, Agent, or Firm* — Mintz, Levin, Cohn, Ferris, Glovsky and Popeo, P.C.

(57) ABSTRACT

The present invention relates to the use of a protein as a hydroxylase, a host cell comprising the protein, the use of the protein or host cell in the production of hydroxy-pipecolic acid (HPA), a method of production HPA, methods of producing the protein, a mutant protein and a nucleic acid encoding the mutant protein and a vector comprising a nucleic acid encoding the protein.

13 Claims, 13 Drawing Sheets
Specification includes a Sequence Listing.

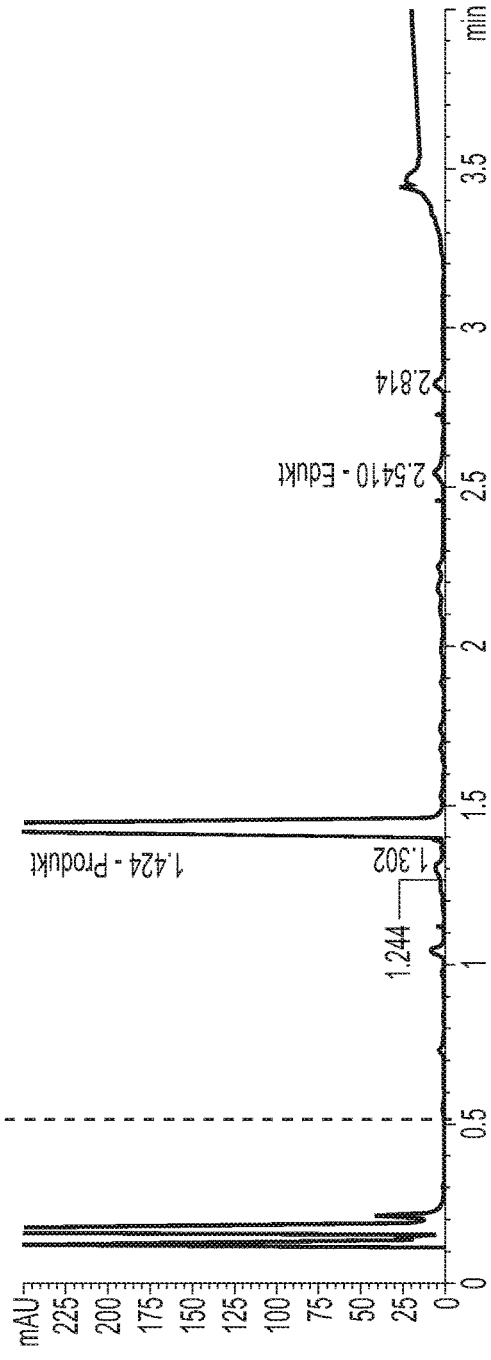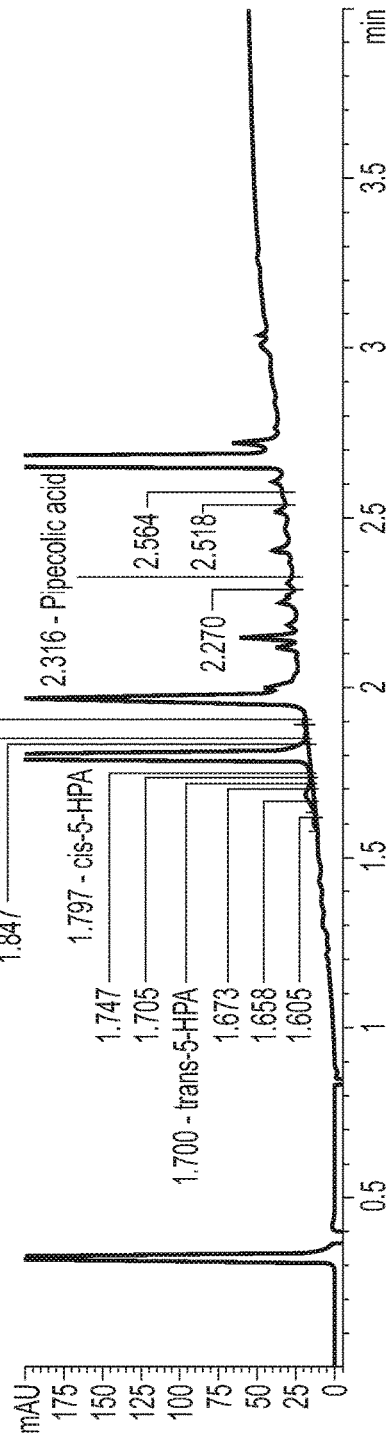

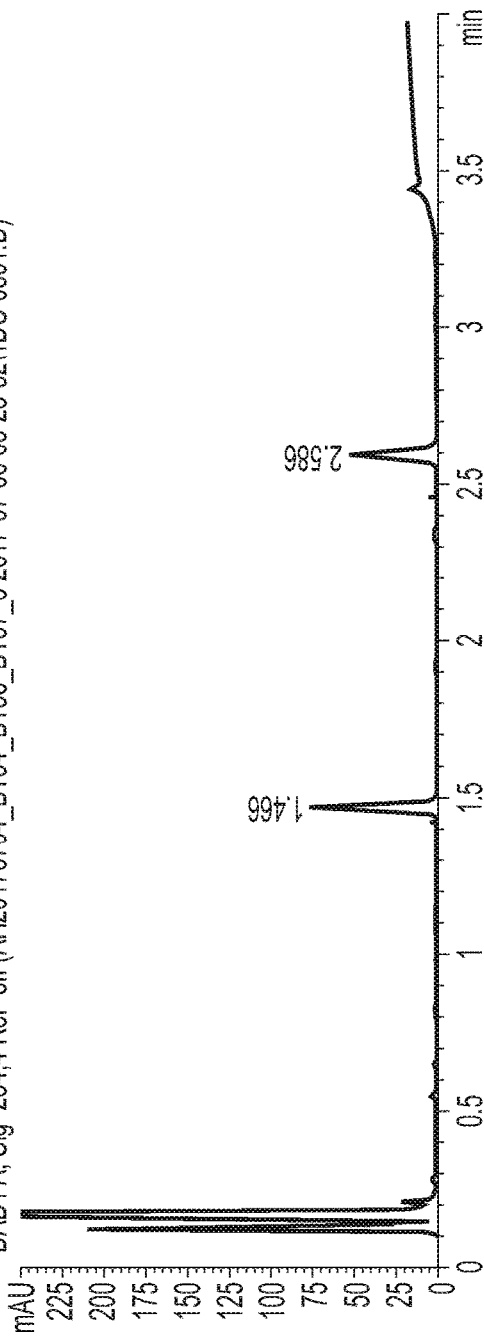
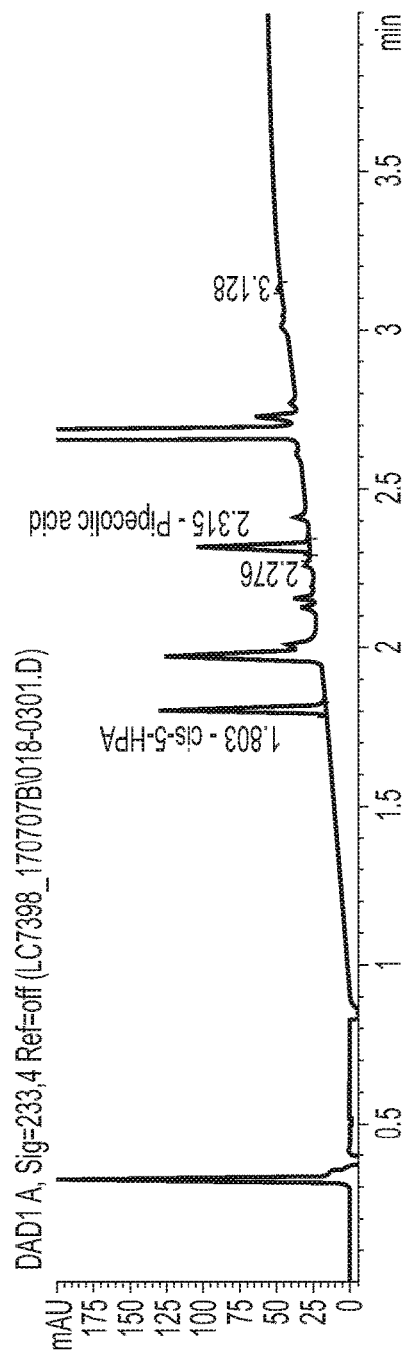
FIG. 5B
FIG. 5C

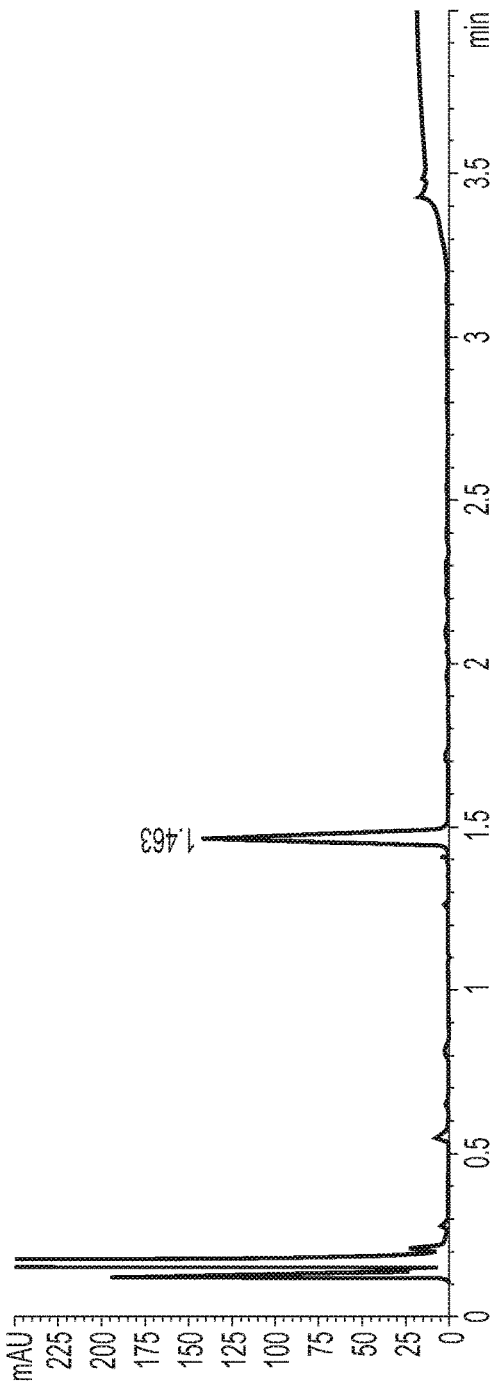
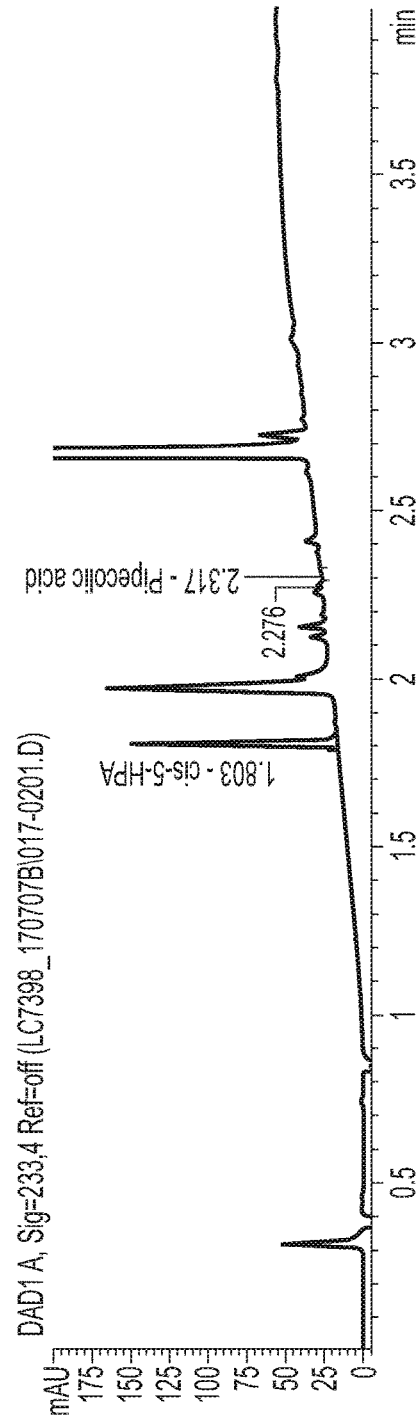
FIG. 7B
FIG. 7C

SEQUENCE LISTING

<160> NUMBER OF SEQ ID NOS: 2

<210> SEQ ID NO 1
<211> LENGTH: 300
<212> TYPE: PRT
<213> ORGANISM: Micromonospora echinospora

<400> SEQUENCE: 1

Met Arg Thr His Tyr Val Ala Thr Val Pro Leu Asp Asp Ala Arg Leu
1               5                   10                  15

Gly Glu Asp Leu Glu Arg Ser Leu Ser Leu Arg Trp Ser Glu Ala Tyr
            20                  25                  30

Ser Asp Tyr Ile Phe Gly Gly Ser Trp Asn Ser Cys Met Leu Trp Ala
        35                  40                  45

Pro Gly Gly Asp Thr Gly Asp Gly Val Val Thr Asn Tyr Ala Tyr Asp
    50                  55                  60

Arg Pro Pro Ala Phe Thr Ala Tyr Ala Asp Gln Leu Pro Tyr Leu Arg
65                  70                  75                  80

Lys Leu Ile Thr Asp Thr Ala Asp Leu Asp Arg Leu Asn Phe Ala Arg
                85                  90                  95

Leu Ala Leu Val Thr Asn Ser Val Gly Ile Pro His Arg Asp Leu Leu
            100                 105                 110

Glu Leu Asp Asp Leu Pro Asn Gln Ser Arg Asn Ala His Arg Met His
        115                 120                 125

Ile Pro Leu Ala Thr Asp Asp Asn Cys Leu Phe Thr Glu Gly Asn Thr
    130                 135                 140

Val Tyr Arg Met Arg Gln Gly Glu Ile Trp Phe Leu Asp Ala Ser Val
145                 150                 155                 160

Ile His Ala Val Ala Val Leu Ser Gly Ile Lys Arg Ile His Leu Met
                165                 170                 175

Leu Asp Phe Val Asp Thr Pro Asp Pro Gly Ser Leu Leu Thr Val Ala
            180                 185                 190

Gly Gly Thr Pro Asp Thr Gly Ile Pro Ala Asp Arg Met Val Ser Arg
        195                 200                 205

Pro Ala Leu Thr Gly Pro Glu Arg Ala Ser Leu Leu Gly Leu Ala Asp
    210                 215                 220

Val Leu Thr Met Asp Thr Phe Asn Glu Val Phe Ser Ile Val Ile Lys
225                 230                 235                 240

Lys His Tyr Arg Ser Asp Gly Asp Asp Phe Val Trp Ser Thr Leu
                245                 250                 255

Ile Asp Leu Ala Arg Gly Ser Ala Asp Pro Ala Val Leu Pro His Ala
            260                 265                 270

Leu Lys Leu Arg Arg Tyr Tyr Thr Leu Glu Arg Ser Ala Gln Glu Leu
        275                 280                 285

Asp Pro Phe Ser Thr Val Asp Pro Ala Val Lys Glu
    290                 295                 300

<210> SEQ ID NO 2
<211> LENGTH: 276
<212> TYPE: PRT
<213> ORGANISM: Kordia jejudonensis

<400> SEQUENCE: 2

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr

-continued

```
                        20                     25                     30
Ser Glu Tyr Ala Ser Gly Ile Trp Lys Thr Cys Met Leu Trp Asn Arg
             35                     40                     45

Ser Gly Gln Lys Asp Asp His Leu Ser Ile Glu His Asp Thr Tyr Val
             50                     55                     60

Lys Pro Thr Glu Tyr Gly Lys Gln Leu Ala Tyr Val Asn Glu Ile Ile
65                      70                     75                     80

Ala Asn Thr Phe Lys Lys Glu His Ile Lys Thr Val Arg Leu Phe Met
                     85                     90                     95

Cys Ile Asn Gly Leu Ile Ile Pro His Lys Asp Tyr Leu Glu Phe Lys
             100                    105                    110

Lys Gly Phe Thr Arg Ile His Ile Pro Leu Lys Ile Asn Glu His Ala
             115                    120                    125

Leu Thr Ser Glu Glu Asp Val Val Tyr Asn Met Gln Lys Gly Glu Ile
             130                    135                    140

Trp Phe Ile Glu Gly Arg Lys Ile His Ser Ala Ala Asn Phe Ser Lys
145                    150                    155                    160

Val Lys Arg Ile Asn Leu Val Ile Asp Phe Ala Pro Asp Ile Pro Phe
                     165                    170                    175

Glu Glu Leu Phe Leu Asn Ser Glu Asn Tyr Gln Pro Asn Leu Ile Pro
                     180                    185                    190

Lys Ile Ser Gln Arg Thr Gln Leu Lys Glu Glu Glu Leu Gly Tyr Ile
             195                    200                    205

Lys Gly Leu Ser Lys Ile Ile Asn Glu Met Asn Phe Asp Asp Ile Leu
             210                    215                    220

Ser Ile Leu Ser Lys Ile His Phe Tyr Arg Asn Val Ser Ser Glu Leu
225                    230                    235                    240

Val Phe Gly Trp Leu Asp Glu Ile Ala Thr Ala Ser Asn Asn Tyr Asn
                     245                    250                    255

Ile Gln Arg Lys Ala Gln Glu Val Thr Asp Leu Leu Ile Arg Lys Gly
             260                    265                    270

Pro Ile Asn Asn
             275
```

US 10,968,469 B2

PROLINE HYDROXYLASES AS WELL AS USES, METHODS AND PRODUCTS INVOLVING THE SAME

ACKNOWLEDGEMENT OF GOVERNMENT SUPPORT

This invention was made with government support under Contract No. HHSO100201600038C awarded by the U.S. Department of Health and Human Services. The Government has certain rights in the invention.

CROSS-REFERENCE

This application claims foreign priority to EP Application No. 17001927.7, filed Nov. 23, 2017, the contents of which are incorporated herein by reference in their entirety.

BACKGROUND

Cyclic hydroxy-amino acids are adequate building blocks for the development of new therapeutic drug candidates. These compounds are β-turn inducers in the synthesis of peptides and good enzyme inhibitors by themselves. Indeed, stereoselective synthesis of hydroxy-amino acids is a field that has been growing during the last decades because of the potential biological activity of some representatives of this class of compounds, mainly as enzyme inhibitors. Particularly, conformationally constrained hydroxy-amino acids such as the hydroxylated pipecolic acids are very interesting target molecules. For instance, the compound (2S,4R)-4-hydroxy-pipecolic acid is a natural product that has been isolated from *Calliandra pittieri* and *Stophantus scandeus*, and the cis-5-hydroxy-substituted pipecolic acid skeleton is frequently found in alkaloids from microorganisms and also in plants (febrifugine, pseudoconhidrine). Furthermore, a tri-hydroxy-pipecolic acid isolated from the seeds of *Baphia racemosa* proved to have specific human liver beta-glucosidase inhibitory activity.

5-hydroxy-pipecolic acid (HPA) is a versatile building block for the synthesis of pharmacologically active compounds, such as for diazabicyclooctane derivatives which have the potential to act as beta-lactamase inhibitors (see e.g. US Patent Application US 2016/0264573 or PCT Publication WO 02/10172).

In the art, different ways of chemical synthesis of 5-hydroxy-pipecolic acid derivatives and their analogues are known, such as a stereoselective synthesis of N-Boc-protected cis-(2R,3S)-3-hydroxy-pipecolic acid, starting from D-glucose. However, chemical synthesis, particularly regio- or stereoselective synthesis, of hydroxy-pipecolic acid is often ineffective, complicated and expensive. Therefore, the present inventors aimed at providing alternative methods for producing and purifying 5-hydroxy-pipecolic acid, especially cis-5-hydroxy-pipecolic acid, which are based on the use of specific enzymes.

In the present application, two proteins have been identified, which surprisingly show hydroxylase activity. Particularly, it could be shown that two enzymes referred to as PH05 and PH12 were characterized by pipecolic acid hydroxylase activity, particularly L-pipecolic acid hydroxylase activity, as well as good regio-selectivity for 5-HPA and stereo-selectivity for cis-5-HPA, particularly (2S,5S)-cis-5-HPA.

SUMMARY

The present invention relates to the use of a protein as a hydroxylase, a host cell comprising the protein, the use of the protein or host cell in the production of hydroxy-pipecolic acid (HPA), a method of production HPA, methods of producing the protein, a mutant protein and a nucleic acid encoding the mutant protein and a vector comprising a nucleic acid encoding the protein.

In an aspect, the present application provides a method of hydroxylation with a hydroxylase protein. In another aspect, the application provides use of a protein as a hydroxylase. In an embodiment, the protein comprises: the polypeptide of SEQ ID NO: 1 or a functionally active variant thereof having pipecolic acid hydroxylase activity, wherein the functionally active variant has at least 75% sequence identity to the polypeptide of SEQ ID NO: 1; and/or the polypeptide of SEQ ID NO: 2 or a functionally active variant thereof having pipecolic acid hydroxylase activity, wherein the functionally active variant has at least 75% sequence identity to the polypeptide of SEQ ID NO: 2.

In an embodiment, the method of hydroxylation or use of a protein as a hydroxylase comprises the functionally active variant of the polypeptide of SEQ ID NO: 1 has at least 80% sequence identity to the polypeptide of SEQ ID NO: 1, preferably at least 85% sequence identity to the polypeptide of SEQ ID NO: 1, more preferably at least 90% sequence identity to the polypeptide of SEQ ID NO: 1, most preferably at least 95% sequence identity to the polypeptide of SEQ ID NO: 1; or wherein the functionally active variant of the polypeptide of SEQ ID NO: 2 has at least 80% sequence identity to the parental polypeptide of SEQ ID NO: 2, preferably at least 85% sequence identity to the polypeptide of SEQ ID NO: 2, more preferably at least 90% sequence identity to the polypeptide of SEQ ID NO: 2, most preferably at least 95% sequence identity to the polypeptide of SEQ ID NO: 2.

In an embodiment, the method or use according to any one of the preceding aspects and embodiments, wherein the protein comprises or consists of the polypeptide of SEQ ID NO: 1 or 2. In another embodiment, the method or use according to any one of the preceding aspects and embodiments, wherein the protein comprises or consists of the polypeptide of SEQ ID NO: 1.

In an embodiment, the method or use according to any one of the preceding aspects and embodiments, wherein the protein is capable of hydroxylating pipecolic acid (PA), particularly L-pipecolic acid (L-PA), to hydroxy-pipecolic acid (HPA), particularly 5-hydroxy-pipecolic acid (5-HPA), more particularly cis-5-hydroxy-pipecolic acid (cis-5-HPA), even more particularly to (2S,5S)-cis-5-hydroxy-pipecolic acid ((2S,5S)-cis-5-HPA). In a further embodiment, the method or use of the protein capable of hydroxylation wherein the protein is characterized by (i) a regio selectivity for 5-HPA of at least 90%, especially at least 95%, more preferably at least 99%; (ii) a stereoselectivity for cis-5-HPA of at least 90%, especially at least 95%, more preferably at least 99%; and/or (iii) a conversion ratio of at least 60%, preferably at least 70%, more preferably at least 75%, most preferably at least 95%.

In an aspect, the present application provides a host cell comprising: (a) the polypeptide of SEQ ID NO: 1 as defined in any of the preceding aspects and embodiments or a nucleic acid encoding the polypeptide, wherein the cell is not a *Micromonospora echinospora* cell, particularly not a *Micromonospora* cell, more particularly not a Micromonosporaceae cell, still more particularly not a Micromonosporales cell, even more particularly not an Actinobacteria cell, especially not a bacterial cell; or (b) the polypeptide of SEQ ID NO: 2 as defined in any of the preceding aspects and embodiments or a nucleic acid encoding the polypeptide, wherein the cell is not a *Kordia jejundanensis* cell, particularly not a *Kordia* cell, more particularly not a Flavobacteriaceae cell, still more particularly not a Flavobacteriales cell, even more particularly not an Bacteroidetes cell, especially not a bacterial cell; or (c) a protein comprising (i) the polypeptide of SEQ ID NO: 1 as defined in any of the preceding aspects and embodiments and at least one additional amino acid or (ii) a functionally active variant of the polypeptide of SEQ ID NO: 1 as defined in any of the preceding aspects and embodiments or a nucleic acid encoding the protein, in particular wherein the cell is not a *Micromonospora echinospora* cell, particularly not a *Micromonospora* cell, more particularly not a Micromonosporaceae cell, still more particularly not a Micromonosporales cell, even more particularly not an Actinobacteria cell, especially not a bacterial cell; or (d) a protein comprising (i) the polypeptide of SEQ ID NO: 2 as defined in any of the preceding aspects and embodiments and at least one additional amino acid or (ii) a functionally active variant of the polypeptide of SEQ ID NO: 2 as defined in any of the preceding aspects and embodiments or a nucleic acid encoding the protein, in particular wherein the cell is not a *Kordia jejundanensis* cell, particularly not a *Kordia* cell, more particularly not a Flavobacteriaceae cell, still more particularly not a Flavobacteriales cell, even more particularly not an Bacteroidetes cell, especially not a bacterial cell. In an embodiment, the host cell is a eukaryotic cell, particularly an animal cell, a plant cell or a fungal cell or wherein the host cell is a prokaryotic cell, in which the protein, polypeptide or nucleic acid according to any one of the host cell definitions above does naturally not occur.

In an embodiment, the present application provides the method or use of the protein as defined above in the preceding aspects and embodiments or the host cell according to any one of the definitions above in the production of HPA, particularly 5-HPA, more particularly cis-5-HPA, even more particularly (2S,5S)-cis-5-hydroxy-pipecolic acid ((2S,5S)-cis-5-HPA).

In an embodiment, the application provides a method of producing HPA, the method comprising hydroxylating PA, particularly L-PA, with a protein as defined according to any one of the preceding aspects or embodiments in the presence of oxygen. In another embodiment, the method produces HPA, wherein HPA is 5-HPA, particularly cis-5-HPA, even more particularly (2S,5S)-cis-5-HPA. In a further embodiment, the protein used for producing HPA is produced in the host cell as defined according to one of the aspects or embodiments above. In an embodiment, the method wherein the hydroxylation takes place in the presence of an oxygen acceptor/co-substrate, particularly α-ketoglutarate and in the presence of $Fe^{2+}$. In another embodiment, the method wherein the hydroxylation takes place in an aqueous environment having a pH 4.5 to 8 at a temperature of 5° C. to 30° C. and/or at an α-ketoglutarate concentration of from 50 to 500 mM with a PA, particularly L-PA, concentration of from 25 mM to 200 mM.

In an embodiment of any one of the preceding methods the method optionally comprises isolating HPA, particularly cis-5-HPA or even more particularly (2S,5S)-cis-5-HPA.

In an aspect, the present application provides a method of producing the protein according to any one of the preceding aspects or embodiments, the method comprising: (a) introducing a vector comprising a nucleic acid encoding the protein as defined according to any one of the preceding aspects into a host cell, particularly in the host cell as defined above, (b) growing the host cell under conditions allowing for expression of the protein as defined according to any one of the preceding aspects, (c) optionally isolating the protein from the host cell.

In another aspect, the present application provides a protein comprising or consisting of: the polypeptide of SEQ ID NO: 1 and at least one additional amino acid, especially at the C and/or N terminus; the polypeptide of SEQ ID NO: 2 and at least one additional amino acid, especially at the C and/or N terminus; a functionally active variant of the polypeptide of SEQ ID NO: 1, differing from the polypeptide of SEQ ID NO: 1 by at least one amino acid residue, but having at least 75% sequence identity to the polypeptide of SEQ ID NO: 1 and having pipecolic acid hydroxylase activity; or a functionally active variant of the polypeptide of SEQ ID NO: 2, differing from the polypeptide of SEQ ID NO: 2 by at least one amino acid residue, but having at least 75% sequence identity to the polypeptide of SEQ ID NO: 2 and having pipecolic acid hydroxylase activity, particularly wherein the protein is further characterized according to one of the preceding embodiments.

In an aspect, the present application provides a nucleic acid coding for the protein according to the previous aspect.

In another aspect, the present application provides a vector comprising the nucleic acid according to the preceding aspect or a nucleic acid encoding the protein as defined according to any of the preceding embodiments.

Accordingly, it is an object of the invention not to encompass within the invention any previously known product, process of making the product, or method of using the product such that Applicants reserve the right and hereby disclose a disclaimer of any previously known product, process, or method.

BRIEF DESCRIPTION OF THE DRAWINGS

The following detailed description, given by way of example, but not intended to limit the invention solely to the specific embodiments described, may best be understood in conjunction with the accompanying drawings.

FIG. 2A shows the conversion of PA 1 to 5-HPA 2 after different reaction times. After 68.5 h 93% of PA 1 (3 mmol) was converted to 5-HPA 2. Additional 1.5 mmol PA 1 (0.5× initial amount) and 3 mmol αKG were added to the reaction mixture. A conversion of PA 1 to 5-HPA 2 of >98% was detected after a total reaction time of 89 h. Conversions were determined by HPLC-analysis. FIG. 2B shows a chromatogram of the reaction mixture after 89 h using dansylchloride derivatization to determine the conversion of L-PA 1 to HPA 2. In the chromatogram of the 89 h sample only traces of the substrate PA 1 is left. FIG. 2C shows a chromatogram of the reaction mixture after 89 h using Fmoc derivatization to determine the diastereomeric excess of the product 2.

FIGS. 3A-3C illustrate preparative scale biotransformation using proline hydroxylase PH05 at various conditions. FIGS. 3A-3C show the results of Example 3. FIG. 3A shows the conversion of PA 1 to 5-HPA 2 after different reaction times, FIG. 3B shows determination of the conversion of L-PA 1 to HPA 2 using dansylchloride derivatization and FIG. 3C shows determination of the diastereomeric excess of the product 2 using Fmoc derivatization (see FIG. 2).

FIGS. 4A-4C show the results of Example 4. FIG. 4A shows the conversion of PA 1 to 5-HPA 2 after different reaction times, FIG. 4B shows determination of the conversion of L-PA 1 to HPA 2 using dansylchloride derivatization and FIG. 4C shows determination of the diastereomeric excess of the product 2 using Fmoc derivatization (see FIG. 2).

FIGS. 5A-5C illustrate preparative scale biotransformation using proline hydroxylase PH05 at various conditions. FIGS. 5A-5C show the results of Example 5. FIG. 5A shows the conversion of PA 1 to 5-HPA 2 after different reaction times, FIG. 5B shows determination of the conversion of L-PA 1 to HPA 2 using dansylchloride derivatization and FIG. 5C shows determination of the diastereomeric excess of the product 2 using Fmoc derivatization (see FIG. 2).

FIGS. 6A-6C show the results of Example 6. FIG. 6A shows the conversion of PA 1 to 5-HPA 2 after different reaction times, FIG. 6B shows determination of the conversion of L-PA 1 to HPA 2 using dansylchloride derivatization and FIG. 6C shows determination of the diastereomeric excess of the product 2 using Fmoc derivatization (see FIG. 2).

FIGS. 7A-7C illustrate preparative scale biotransformation using proline hydroxylase PH12 at various conditions. FIGS. 7A-7C show the results of Example 7. FIG. 7A shows the conversion of PA 1 to 5-HPA 2 after different reaction times, FIG. 7B shows determination of the conversion of L-PA 1 to HPA 2 using dansylchloride derivatization and FIG. 7C shows determination of the diastereomeric excess of the product 2 using Fmoc derivatization (see FIG. 2).

DETAILED DESCRIPTION

Figure 1:
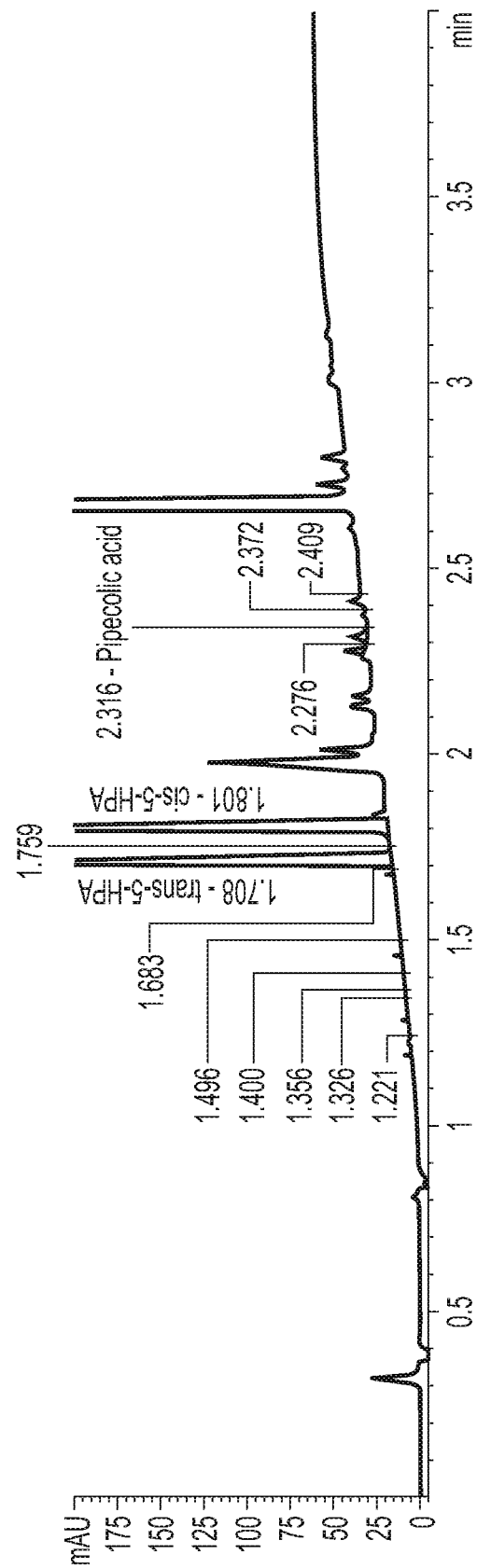
FIG. 1 illustrates a reference chromatogram of reference standards of cis-5-HPA and the corresponding diastereomer trans-5-HPA.

The present invention relates to the use of a protein as a hydroxylase, wherein the protein comprises the polypeptide of SEQ ID NO: 1 or a functionally active variant thereof having pipecolic acid hydroxylase activity, wherein the functionally active variant has at least 75% sequence identity to the polypeptide of SEQ ID NO: 1; and/or the polypeptide of SEQ ID NO: 2 or a functionally active variant thereof having pipecolic acid hydroxylase activity, wherein the functionally active variant has at least 75% sequence identity to the polypeptide of SEQ ID NO: 2.

Enzymes are macromolecular biological catalysts, usually proteins, and accelerate chemical reactions. The molecules upon which enzymes may act are substrates and the enzyme converts the substrates into products. Like all catalysts, enzymes increase the reaction rate by lowering its activation energy.

A hydroxylase is an enzyme capable of catalyzing a reaction that introduces a hydroxyl group (—OH) into a compound. Hydroxylation is often the first step in the oxidative degradation of organic compounds. Hydroxylases are usually categorized based on the compound to be hydroxylated. The present hydroxylase hydroxylates proline; accordingly, the enzyme is referred to as proline hydroxylase. The proline hydroxylases are α-ketoglutarate-dependent dioxygenases using $Fe^{2+}$ in their active site for the hydroxylation reaction. Dioxygenases, or oxygen transferases, use molecular oxygen for the hydroxylation and incorporate both atoms of molecular oxygen ($O_2$) into the product(s) of the reaction. With proline hydroxylases, the first oxygen is usually transferred to the co-substrate α-ketoglutarate, which is converted to succinate and the second oxygen atom is transferred to proline. Often ascorbic acid (vitamin C) is used to return the iron to its reduced form (Fe (II)).

In accordance with the present application, the proteins as defined herein in accordance with the present invention are used as a hydroxylase. This means that the protein is contacted with a substrate to be hydroxylated under conditions allowing hydroxylation and hydroxylation takes place. The protein comprises a polypeptide of SEQ ID NO: 1 or 2 or a variant thereof, as defined herein.

The polypeptides of SEQ ID NO: 1 and SEQ ID NO: 2 are referred to as wild-type, show proline hydroxylase activity and may thereby be used as hydroxylases.

The polypeptide of SEQ ID NO:1 is derived from *Micromonospora echinospora* (*Micromonospora purpurea*) and has the following amino acid sequence:

```
                                                         (SEQ ID NO: 1)
MRTHYVATVP LDDARLGEDL ERSLSLRWSE AYSDYIFGGS WNSCMLWAPG GDTGDGVVTN  60

YAYDRPPAFT AYADQLPYLR KLITDTADLD RLNFARLALV TNSVGIPHRD LLELDDLPNQ 120

SRNAHRMHIP LATDDNCLFT EGNTVYRMRQ GEIWFLDASV IHAVAVLSGI KRIHLMLDFV 180

DTPDPGSLLT VAGGTPDTGI PADRMVSRPA LTGPERASLL GLADVLTMDT FNEVFSIVIK 240

KHYRSDGGDD FVWSTLIDLA RGSADPAVLP HALKLRRYYT LERSAQELDP FSTVDPAVKE 300
```

*Micromonospora echinospora* is a gram-positive, spore-forming, generally aerobic bacterial strain, which forms a branched mycelium and occurs as saprotrophic forms in soil and water. The species is known for producing the enediyne antibiotic calicheamicins. The scientific classification is as follows:

Kingdom: Bacteria
Phylum: Actinobacteria
Order: Actinomycetales
Family: Micromonosporaceae
Genus: *Micromonospora*
Species: *echinospora*

The polypeptide of SEQ ID NO:2 is derived from *Kordia jejudonensis* and has the following amino acid sequence:

```
                                                          (SEQ ID NO: 2)
MESKIIGKVN FEEHLLDKEL KLIDTFEFND SYSEYASGIW KTCMLWNRSG QKDDHLSIEH  60

DTYVKPTEYG KQLAYVNEII ANTFKKEHIK TVRLFMCING LIIPHKDYLE FKKGFTRIHI 120
```

```
-continued
PLKINEHALT SEEDVVYNMQ KGEIWFIEGR KIHSAANFSK VKRINLVIDF APDIPFEELF    180

LNSENYQPNL IPKISQRTQL KEEELGYIKG LSKIINEMNF DDILSILSKI HFYRNVSSEL    240

VFGWLDEIAT ASNNYNIQRK AQEVTDLLIR KGPINN                              276
```

*Kordia jejudonensis* is a Gram-staining-negative, aerobic, non-spore-forming, non-flagellated, non-gliding and rod-shaped bacterial strain, which was isolated from the zone where the ocean and a freshwater spring meet at Jeju island, South Korea (Park et al, 2014, Int J Syst Evol Microbiol 64: 657-662). The scientific classification is as follows:
Kingdom: Bacteria
Phylum: Bacteroidetes
Order: Flavobacteriales
Family: Flavobacteriaceae
Genus: *Kordia*
Species: *jejundanensis*

The polypeptides of SEQ ID NO: 1 and SEQ ID NO: 2 show pipecolic acid hydroxylase activity. This means that these polypeptides are capable of hydroxylating pipecolic acid (PA), particularly L-pipecolic acid (L-PA), to hydroxy-pipecolic acid (HPA), preferably 5-hydroxy-pipecolic acid (5-HPA), as shown in the following scheme 1:

Scheme 1

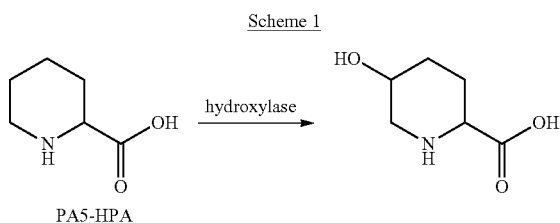 [SMILES: O=C(O)C1CCCCN1 ; O=C(O)C1CCC(O)CN1]

PA5-HPA

In accordance with the present invention, the protein comprises the polypeptide of SEQ ID NO: 1 and/or 2 (wild-type) or a functionally active variant thereof, wherein the functionally active variant differs from the wild-type by at least one amino acid, but has pipecolic acid hydroxylase activity, i.e. it is capable of hydroxylating pipecolic acid (PA), particularly L-pipecolic acid (L-PA), to hydroxy-pipecolic acid (HPA), preferably 5-hydroxy-pipecolic acid (5-HPA). Due to their enzymatic activity also these variants may be used as hydroxylases in the present invention. The functionally active variant according to the present invention having pipecolic acid hydroxylase activity has at least 75% and 75% sequence identity to the polypeptide of SEQ ID NO: 1 and 2, respectively.

Enzymatic activity is a measure of the activity of enzyme. The SI unit for enzyme activity is katal (1 katal=1 mol s$^{-1}$). A more practical and commonly used value is enzyme unit (U)=1 µmol min$^{-1}$. 1 U corresponds to 16.67 nanokatals. One U is defined as the amount of the enzyme that catalyzes the conversion of 1 micro mole of substrate per minute. The conditions when measuring the activity are usually standardized: one usually takes a temperature of 25° C. or 30° C. and the pH value and substrate concentration that yields the maximal substrate conversion rate. The specific activity of an enzyme is the activity of an enzyme per milligram of total protein (expressed in µmol min$^{-1}$mg$^{-1}$). It is the amount of product formed by an enzyme in a given amount of time under given conditions per milligram of total protein. Specific activity is equal to the rate of reaction multiplied by the volume of reaction divided by the mass of total protein. The SI unit is katal kg$^{-1}$, but a more practical unit is µmol min$^{-1}$ mg$^{-1}$. Specific activity is a measure of enzyme processivity, at a specific (usually saturating) substrate concentration, and is usually constant for a pure enzyme. If the molecular weight of the enzyme is known, the turnover number, or µmol product sec$^{-1}$ µmol$^{-1}$ of active enzyme, can be calculated from the specific activity. The turnover number can be visualized as the number of times each enzyme molecule carries out its catalytic cycle per second.

The activity may be determined in an enzyme assay measuring either the consumption of substrate or production of product over time. A large number of different methods of measuring the concentrations of substrates and products exist and many enzymes can be assayed in several different ways as known to the person skilled in the art. In the present invention, the protein in question is incubated with PA, particularly L-PA, under conditions (e.g. presence of $O_2$, $Fe^{2+}$, α-ketoglutarate and optionally ascorbic acid) and for a time conducive to the hydroxylation. Suitable conditions and times are given in the Examples.

Methods of determining enzymatic activity including hydroxylase activity, particularly pipecolic acid hydroxylase activity, are well-known to the person skilled in the art. Exemplary methods are also described in the Examples.

In a preferred embodiment of the present invention, the functionally active variant of the polypeptide of SEQ ID NO: 1 has at least 5% of the pipecolic acid hydroxylase activity of the polypeptide of SEQ ID NO: 1 (i.e. the corresponding wild-type), more preferably at least 10%, 20%, 30%, 40%, 50%, 60% or 70%, still more preferably at least 75%, even more preferably at least 80%, most preferably at least 90% of the pipecolic acid hydroxylase activity of the polypeptide of SEQ ID NO: 1.

In another preferred embodiment of the present invention, the functionally active variant of the polypeptide of SEQ ID NO: 2 has at least 5% of the pipecolic acid hydroxylase activity of the polypeptide of SEQ ID NO: 2 (i.e. the corresponding wild-type), more preferably at least 10%, 20%, 30%, 40%, 50%, 60% or 70%, still more preferably at least 75%, even more preferably at least 80%, most preferably at least 90% of the pipecolic acid hydroxylase activity of the polypeptide of SEQ ID NO: 2.

Additionally, the functionally active variants are characterized by a defined sequence identity of at least 75% and 75% sequence identity to the polypeptide of SEQ ID NO: 1 and 2, respectively. The term "at least X % identical" or "at least X % sequence identity" as used herein means that the sequence of the variant according to the present invention has an amino acid sequence characterized in that, within a stretch of 100 amino acids, at least X amino acids residues are identical to the sequence of the corresponding wild-type sequence, i.e. the sequence of SEQ ID NO: 1 or 2. Sequence identity according to the present invention can, e.g., be determined by methods of sequence alignment in form of sequence comparison. Methods of sequence alignment are well known in the art and include various programs and alignment algorithms which have been described in, e.g., Pearson and Lipman (1988). Moreover, the NCBI Basic Local Alignment Search Tool (BLAST) is available from several sources, including the National Center for Biotechnology Information (NCBI, Bethesda, Md.) and on the internet, for use in connection with the sequence analysis programs blastp, blastn, blastx, tblastn and tblastx. Percentage of identity of mutants according to the present invention relative to the amino acid sequence of SEQ ID NO: 1 or 2 is typically characterized using the NCBI Blast blastp with standard settings. Alternatively, sequence identity may be determined using the software GENEious with standard settings.

The variant according to the present invention may comprise one or more amino acid deletion(s), particularly small (e.g. up to 10 amino acids) N- and/or C-terminal deletions, one or more additions, particularly small (e.g. up to 10 amino acids) N- and/or C-terminal additions, one or more substitutions, particularly one or more conservative amino acid substitutions, or combinations thereof. Conservative amino acid substitution refers to a substitution of a residue with a different residue having a similar side chain, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, and isoleucine; an amino acid with hydroxyl side chain is substituted with another amino acid with a hydroxyl side chain, e.g., serine and threonine; an amino acid having aromatic side chains is substituted with another amino acid having an aromatic side chain, e.g., phenylalanine, tyrosine, tryptophan, and histidine; an amino acid with a basic side chain is substituted with another amino acid with a basic side chain, e.g., lysine and arginine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively. Examples of conservative amino acid substitutions include those listed below:

| Original Residue | Conservative Substitutions |
|---|---|
| Ala, Leu, Val, Ile | Other aliphatic (Ala, Leu, Val, Ile) |
| | Other non-polar (Ala, Leu, Val, Ile, Gly, Met) |
| Gly, Met | Other non-polar (Ala, Leu, Val, Ile, Gly, Met) |
| Asp, Glu | Other acidic (Asp, Glu) |
| Lys, Arg | Other basic (Lys, Arg) |
| Asn, Gln, Ser, Thr | Other polar (Asn, Gln, Ser, Thr) |
| His, Tyr, Trp, Phe | Other aromatic (His, Tyr, Trp, Phe) |
| Cys, Pro | None |

In one embodiment of the present invention, the variant according to the present invention may comprise up to 50, 40, 30, 20, especially 10, additions, deletions, and/or substitutions.

In a preferred embodiment, the functionally active variant of the polypeptide of SEQ ID NO: 1 has at least 80% sequence identity to the polypeptide of SEQ ID NO: 1, preferably at least 85% sequence identity to the polypeptide of SEQ ID NO: 1, more preferably at least 90% sequence identity to the polypeptide of SEQ ID NO: 1, most preferably at least 95% sequence identity to the polypeptide of SEQ ID NO: 1; or wherein the functionally active variant of the polypeptide of SEQ ID NO: 2 has at least 80% sequence identity to the parental polypeptide of SEQ ID NO: 2, preferably at least 85% sequence identity to the polypeptide of SEQ ID NO: 2, more preferably at least 90% sequence identity to the polypeptide of SEQ ID NO: 2, most preferably at least 95% sequence identity to the polypeptide of SEQ ID NO: 2. The sequence identity may be determined as detailed above. More preferably, the functionally active variant of the polypeptide of SEQ ID NO: 1 has at least 96% sequence identity to the polypeptide of SEQ ID NO: 1, preferably at least 97% sequence identity to the polypeptide of SEQ ID NO: 1, more preferably at least 98% sequence identity to the polypeptide of SEQ ID NO: 1, most preferably at least 99% sequence identity to the polypeptide of SEQ ID NO: 1; or wherein the functionally active variant of the polypeptide of SEQ ID NO: 2 has at least 96% sequence identity to the parental polypeptide of SEQ ID NO: 2, preferably at least 97% sequence identity to the polypeptide of SEQ ID NO: 2, more preferably at least 98% sequence identity to the polypeptide of SEQ ID NO: 2, most preferably at least 99% sequence identity to the polypeptide of SEQ ID NO: 2.

The functionally active variant of the polypeptide of SEQ ID NO: 1 are preferred over the functionally active variant of the polypeptide of SEQ ID NO: 2.

Most preferably, the protein comprises or consists of the polypeptide of SEQ ID NO: 1 or 2, even more preferably of the polypeptide of SEQ ID NO: 1.

The protein comprising the polypeptide of SEQ ID NO: 1 or 2 or a functionally active variant thereof may be used as a hydroxylase, i.e. as an enzyme catalyzing the introduction of a hydroxyl group (—OH) into a compound. For this the compound to be hydroxylated is incubated with the protein under conditions (e.g. presence of $O_2$, $Fe^{2+}$, α-ketoglutarate and optionally ascorbic acid) and for a time conducive to the hydroxylation. The compound to be hydroxylated is preferably pipecolic acid (PA), particularly L-pipecolic acid (L-PA), and the product is hydroxy-pipecolic acid (HPA), especially 5-hydroxy-pipecolic acid (5-HPA), particularly cis-5-hydroxy-pipecolic acid (cis-5-HPA), even more particularly to (2S,5S)-cis-5-hydroxy-pipecolic acid ((2S,5S)-cis-5-HPA).

In accordance with this, the protein used as hydroxylases is capable of hydroxylating pipecolic acid (PA), particularly L-pipecolic acid (L-PA), to hydroxy-pipecolic acid (HPA), particularly 5-hydroxy-pipecolic acid (5-HPA). In certain embodiments, it may be desirable to produce isomers or stereospecific products. Therefore, the protein used as hydroxylases is more particularly capable of hydroxylating pipecolic acid (PA) to cis-5-hydroxy-pipecolic acid (cis-5-HPA), even more particularly to (2S,5S)-cis-5-hydroxy-pipecolic acid ((2S,5S)-cis-5-HPA).

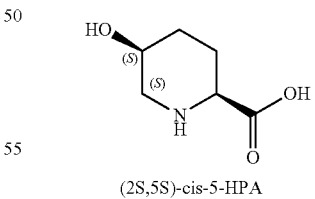

(2S,5S)-cis-5-HPA

In a further preferred embodiment, the protein is characterized by
i) a regioselectivity for 5-HPA of at least 90%, especially at least 95%, more preferably at least 99%;
ii) a stereoselectivity for cis-5-HPA of at least 90%, especially at least 95%, more preferably at least 99%; and/or
iii) a conversion ratio of at least 60%, preferably at least 70%, more preferably at least 75%, most preferably at least 95%.

As detailed above, it may be desirable to hydroxylate PA, particularly L-PA, specifically in order to obtain products characterized by a particular specificity.

In one embodiment, it is intended to hydroxylate PA regioselectively. Particularly, it may be desirable to produce 5-HPA rather than e.g. 3-hydroxy-pipecolic acid (3-HPA) or a mixture thereof. Therefore, a protein characterized by a regioselectivity for 5-HPA of at least 90%, especially at least 95%, more preferably at least 99%, is preferred.

The term "at least X % regioselectivity" as used herein means that of 100 HPA molecules produced according to the present invention, at least X molecules are 5-HPA. In order to determine the percentage of regioselectivity, the HPA molecules produced in the enzymatic reaction may be analysed for the position of the hydroxyl group in the carbon ring and the amount of the compounds may be determined, e.g. by HPLC analysis (see Examples).

In another embodiment, it is intended to hydroxylate PA, particularly L-PA, stereoselectively. Particularly, it may be desirable produce cis-5-HPA rather than e.g. trans-5-HPA or a mixture thereof. Therefore, a protein characterized by a stereoselectivity for cis-5-HPA of at least 90%, especially at least 95%, more preferably at least 99%, is preferred.

The term "at least X % stereoselectivity" as used herein means that of 100 5-HPA molecules produced according to the present invention, at least X molecules are cis-5-HPA. In order to determine the percentage of stereoselectivity, the 5-HPA molecules produced in the enzymatic reaction may be analysed for their configuration and the amount of the compounds may be determined, e.g. by HPLC analysis (e.g. as detailed in the Examples).

In still another embodiment, it may be intended to obtain high yields of product. Particularly, it may be desirable produce a high amount of 5-HPA, especially cis-5-HPA. Therefore, a protein characterized by a conversion ratio of at least 60%, preferably at least 70%, more preferably at least 75%, most preferably at least 95%, is preferred.

The term "conversion ratio of at least X %" as used herein means that of 100 substrates (e.g. PA) at least X products are produced according to the present invention. In order to determine the conversion ratio, the number of products and/or substrates of the enzymatic reaction may be determined, e.g. by HPLC analysis (e.g. as detailed in the Examples). Often the number of substrates prior to the reaction is known and may be compared to the number of products obtained. Alternatively, the number of substrates after the reaction may be determined and used to calculate the number or products by subtracting the number of substrates after the reaction from the number of substrates prior to the reaction.

In another aspect, the present invention relates to a host comprising a protein comprising a. the polypeptide of SEQ ID NO: 1 as defined above or a nucleic acid encoding the polypeptide, wherein the cell is not a *Micromonospora echinospora* cell, particularly not a *Micromonospora* cell, more particularly not a Micromonosporaceae cell, still more particularly not a Micromonosporales cell, even more particularly not an Actinobacteria cell, especially not a bacterial cell; or b. the polypeptide of SEQ ID NO: 2 as defined above or a nucleic acid encoding the polypeptide, wherein the cell is not a *Kordia jejundanensis* cell, particularly not a *Kordia* cell, more particularly not a Flavobacteriaceae cell, still more particularly not a Flavobacteriales cell, even more particularly not an Bacteroidetes cell, especially not a bacterial cell; or c. a protein comprising (i) the polypeptide of SEQ ID NO: 1 as defined above and at least one additional amino acid or (ii) a functionally active variant of the polypeptide of SEQ ID NO: 1 as defined above or a nucleic acid encoding the protein, in particular wherein the cell is not a *Micromonospora echinospora* cell, particularly not a *Micromonospora* cell, more particularly not a Micromonosporaceae cell, still more particularly not a Micromonosporales cell, even more particularly not an Actinobacteria cell, especially not a bacterial cell; or d. a protein comprising (i) the polypeptide of SEQ ID NO: 2 as defined above and at least one additional amino acid or (ii) a functionally active variant of the polypeptide of SEQ ID NO: 2 as defined in above or a nucleic acid encoding the protein, in particular wherein the cell is not a *Kordia jejundanensis* cell, particularly not a *Kordia* cell, more particularly not a Flavobacteriaceae cell, still more particularly not a Flavobacteriales cell, even more particularly not an Bacteroidetes cell, especially not a bacterial cell.

A host cell is a cell in which a foreign molecule, i.e. a molecule not naturally occurring in that cell, has been introduced. In the present invention, this may be an amino acid or a nucleic acid capable of being expressed in the cell to produce the corresponding protein.

As detailed above, the polypeptides of sequences of SEQ ID NO:1 and SEQ ID NO:2 are derived from naturally occurring organisms, particularly from *Micromonospora echinospora* and from *Kordia jejundanensis*, respectively.

As soon as the polypeptide of the sequence of SEQ ID NO:1 or the polypeptide of the sequence of SEQ ID NO:2 is transferred to a cell other than a cell naturally comprising the polypeptide in question, a host cell according to the present invention is obtained.

Moreover, as soon as a protein differing from the polypeptide of the sequence of SEQ ID NO:1 and from the polypeptide of the sequence of SEQ ID NO:2 by at least one amino acid, it is no more to be regarded as a naturally occurring protein and may be introduced in any cell in order to obtain a host cell according to the present invention. The difference to the naturally occurring polypeptides of SEQ ID NO: 1 and 2 may be obtained by addition of at least one amino acid. Alternatively or additionally, it may be a variant of polypeptides of SEQ ID: 1 and 2 as defined above.

The host cell may comprise in addition or as an alternative a nucleic acid coding for the polypeptides or proteins described herein, which may be introduced into a host cell.

The host cell of the present invention can be any kind of organism with the above exceptions, that is suitable for application in recombinant DNA technology, and includes, but is not limited to, all sorts of bacterial and yeast strain which are suitable for expressing one or more recombinant protein(s). Examples of host cells include, for example, various *Bacillus subtilis* or *E. coli* strains. A variety of *E. coli* bacterial host cells are known to a person skilled in the art and include, but are not limited to, strains such as BL21 (DE3), DH5-alpha, HB101, MV1190, JM109, JM101, or XL-1 blue which can be commercially purchased from diverse suppliers including, e.g., New England Biolabs (MA, USA), Stratagene (CA, USA), Promega (WI, USA) or Qiagen (Hilden, Germany) A particularly suitable host cell is also described in the Examples, namely *E. coli* BL21 (DE3) cells. *Bacillus subtilis* strains which can be used as a host cell include, e.g., 1012 wild type: leuA8 metB5 trpC2 hsdRM1 and 168 Marburg: trpC2 (Trp-), which are, e.g., commercially available from MoBiTec (Germany).

Methods of introducing amino acid or nucleic acid sequences into a host cell are well known in the art and include techniques such as transformation, particularly chemical transformation, transfection, lipofectin, cytofectin, particle bead bombardment, electroporation, microinjection, or viral infection. The host cells may be transiently transfected or stably transformed cell lines.

In another embodiment, the host cell is a eukaryotic cell, particularly an animal cell (including human), a plant cell or a fungal cell. Examples of such host cells include CHO cells; HeLa cells; liver cells; CV-1 cells; P19 cells; NT2/D1 cells; mouse L cells; African Green monkey kidney cells, such as COS-7 cells or other COS cells; human embryonic kidney cells, such as HEK 293; DG44 cells, ltk– cells, mouse NIH 3T3 cells and yeast cells.

In another preferred embodiment, the host cell is a prokaryotic cell, in which the protein, polypeptide or nucleic acid as defined above in accordance with the present invention does naturally not occur. The prokaryotic cell may be an Archaea cell or a bacterial cell, particularly a cell of a phylum selected from the group consisting of Acidobacteria, Actinobacteria, Aquificae, Bacteroidetes, Chlamydiae, Dictyoglomi, Fibrobacteres, Fusobacteria, Gemmatimonadetes, Lentisphaerae, Planctomycetes, Proteobacteria, Spirochaetes, Tenericutes (Mollicutes), and Verrucomicrobia.

In a further aspect, the present invention relates to the use of the protein or the host cell as defined above in accordance with the present invention in the production of HPA, particularly 5-HPA, more particularly cis-5-HPA, even more particularly (2S,5S)-cis-5-hydroxy-pipecolic acid ((2S,5S)-cis-5-HPA). As detailed above, the protein of the present invention has hydroxylase activity and is preferably capable of hydroxylating PA, particularly L-PA, to HPA particularly 5-HPA, more particularly cis-5-HPA, even more particularly (2S,5S)-cis-5-HPA. Accordingly, it may be used for this purpose. The above and below definitions of the technical terms apply also to this aspect of the invention.

In a further aspect, the present invention relates to a method of producing HPA, the method comprising hydroxylating PA, particularly L-PA, with a protein as defined above in accordance with the present invention in the presence of oxygen. In a preferred embodiment, HPA is 5-HPA, particularly cis-5-HPA, even more particularly (2S,5S)-cis-5-HPA. As detailed above, the protein of the present invention has hydroxylase activity and is capable of hydroxylating PA, particularly L-PA, to HPA, particularly cis-5-HPA, even more particularly (2S,5S)-cis-5-HPA. The above and below definitions of the technical terms apply also to this aspect of the invention.

For the method, PA, particularly L-PA, is contacted with the protein with hydroxylase activity and as defined herein in the presence of oxygen under conditions allowing the hydroxylation of PA, particularly L-PA, to HPA. Usually, the hydroxlyase belongs to the family of α-ketoglutarate-dependent dioxygenases which use molecular oxygen for the hydroxylation. One oxygen atom is transferred to PA to produce HPA and the other oxygen atom of the molecular oxygen is transferred to an acceptor (co-substrate) according to the following scheme:

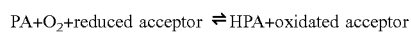

PA+$O_2$+reduced acceptor ⇌ HPA+oxidated acceptor

The acceptor may be any molecule to which the oxygen may be transferred by the protein according to the present invention. Suitable acceptors include α-ketoglutarate, α-ketoadipate and other α-ketodiacid homologs; however, α-ketoglutarate is preferred.

Typically, all reagents are present in a solution and under condition allowing the reaction, which implies suitable reaction conditions as regards, e.g., temperature, pressure, pH, concentrations of various components, presence of co-factors etc. Suitable conditions are illustrated in the examples.

Usually, the assay will be carried out at ambient temperature or another suitable temperature (e.g. 15° C. to 40° C.; such as 15° C., 25° C., or 37° C.), although it can be conducted over a range of temperatures, such as 5° C. to 40° C. It was found that a temperature of 15° C. yielded high conversions, which is surprising, as enzymatic reactions are usually carried out at higher temperatures such as 30° C. to 37° C. Accordingly, a temperature in the range of 10° C. to 30° C. is preferred.

Contacting/incubation time can vary from about 5 minutes to many hours, preferably from about 15 h to 200 h, such as 50 h to 100 h. However, the incubation time will depend upon the assay format, volume of solution, concentrations of substrates and catalysts, the amount of PA to be hydroxylated and the like.

The protein might be applied as solution, lyophilisate, might be immobilized or used as a whole-cell catalyst (see Examples). In a preferred embodiment, the protein is produced in the host cell as defined above. During the method of the invention it may still be contained in the cell (see Examples) or it may have been isolated therefrom.

Preferably, the hydroxylation takes place in the presence of an oxygen acceptor/co-substrate, particularly α-ketoglutarate, and in the presence of $Fe^{2+}$. Oxygen may be provided using a device for gas supply, as known in the art. Oxygen may be supplied in the form of gas, e.g. as air or as an artificial gas such as carbogen (mixture of carbon dioxide and oxygen gas). The gas may be introduced into a solution or suspension, in which all other components of the reaction are contained. $Fe^{2+}$ is usually provided as an soluble, non-toxic salt, suitable examples of which are known in the art, which include ammonium iron(II) sulfate (Mohr salt).

In a preferred embodiment, the hydroxylation takes place in an aqueous environment having a pH of 4.5 to 8 at a temperature of 5° C. to 30° C. and/or at an α-ketoglutarate concentration of from 50 to 500 mM with a PA, particularly L-PA, concentration of from 25 mM to 200 mM. Aeration rates may be in the range of from 50 mL/min up to 250 mL/min.

In one embodiment of the present invention, method of producing HPA comprises isolating HPA, particularly cis-5-HPA or even more particularly (2S,5S)-cis-5-HPA. HPA, particularly cis-5-HPA or even more particularly (2S,5S)-cis-5-HPA may be isolated by any method known in the art including chromatography such as ion exchange chromatography.

In another aspect, the present invention relates to a method of producing the protein as defined above in the context of the present invention, the method comprising expressing a nucleic acid encoding the protein in the host cell, particularly in the host cell as defined above in the context of the present invention.

The expression of nucleic acids in prokaryotic or eukaryotic host cells provides the means for the production of substantial amounts of proteins for commercial and investigational use. A nucleic acid encoding a protein according to the invention can be introduced into a suitable host cell(s) to produce the respective protein by recombinant means. This approach may include the cloning of the respective nucleic acid into a suitable plasmid vector. Plasmid vectors are widely used for gene cloning, and can be easily introduced, i.e. transformed, into cells which have been made transiently permeable to DNA. The host cells comprising the nucleic acid may be cultured in an appropriate medium and the protein according to the present invention may be obtained from the cultured cell or culture medium. The protein according to the present invention may be recovered and optionally purified in the conventional manner, which include methods like precipitation, centrifugation, chromatographic methods, affinity binding (using e.g. tags) etc. The expression of the nucleic acid might be inducible (e.g. by use of an inducible promoter) or constitutive in the host cell.

In a related aspect, the present invention provides a method of producing the protein as defined above in the context of the present invention, the method comprising:
a) introducing a vector comprising a nucleic acid encoding the protein as defined above in the context of the present invention into a host cell, particularly in the host cell as defined above in the context of the present invention,
b) growing the host cell under conditions allowing for expression of the protein as defined above in the context of the present invention,
c) optionally isolating the protein from the host cell.

As a first step, a vector comprising the nucleic acid in question is introduced into a host cell. The person skilled in the art is capable of selecting an appropriate vector-host combination for the expression of an exogenous nucleic acid. There are many molecular tools and protocols at hand for the high-level production of heterologous proteins, such as a vast catalog of expression plasmids, a great number of engineered strains and many cultivation strategies. In order to express the desired amino acid sequence e.g. by introducing a vector comprising the nucleic acid encoding the protein, into a host cell, the vector may contain, in addition to the nucleic acid sequence according to the present invention, other sequences for controlling the expression (e.g., promoter sequences, terminator sequences and enhancer sequences) and gene markers for selecting microorganisms, insect cells, animal culture cells, or the like (e.g., ampicillin, neomycin or kanamycin resistance genes). Furthermore, the vector may contain the nucleic acid sequence according to the present invention in a repeated form (e.g., in tandem). The vector may be constructed based on procedures and manners which are conventionally used in the field of genetic engineering.

As a second step, the host cell is grown under conditions allowing for expression of the protein as defined above in the context of the present invention. The cultivation of host cells according to the invention is a routine procedure known to the skilled person. These host cells can by any kind of suitable cells, preferably bacterial cells such as *E. coli*, particularly *E. coli* BL21(DE3), which can be cultivated in culture.

As a third and optional step, the protein may be isolated from the host cell. After the protein has been expressed in the respective host cell, the cells can be harvested and serve as the starting material for the preparation of a cell extract containing the protein of interest. A cell extract containing the protein of interest is obtained by lysis of the cells. Methods of preparing a cell extract by means of chemical, biological, enzymatic and/or mechanical cell lysis are well known to the person skilled in the art, and include, but are not limited to, e.g. hypotonic salt treatment, homogenization, or ultrasonification. Thereafter the protein may be isolated as detailed with respect to the previous aspect of the invention.

In another aspect, the present invention relates to a protein comprising or consisting of
the polypeptide of SEQ ID NO: 1 and at least one additional amino acid, especially at the C and/or N terminus;
the polypeptide of SEQ ID NO: 2 and at least one additional amino acid, especially at the C and/or N terminus;
a functionally active variant of the polypeptide of SEQ ID NO: 1, differing from the polypeptide of SEQ ID NO: 1 by at least one amino acid residue, but having at least 75% sequence identity to the polypeptide of SEQ ID NO: 1 and having pipecolic acid hydroxylase activity; or
a functionally active variant of the polypeptide of SEQ ID NO: 2, differing from the polypeptide of SEQ ID NO: 2 by at least one amino acid residue, but having at least 75% sequence identity to the polypeptide of SEQ ID NO: 2 and having pipecolic acid hydroxylase activity,
particularly wherein the protein is further characterized as defined above in the context of specific and preferred embodiments of the present invention. In a preferred embodiment, the functionally active variant of the polypeptide of SEQ ID NO: 1 has at least 80% sequence identity to the polypeptide of SEQ ID NO: 1, preferably at least 85% sequence identity to the polypeptide of SEQ ID NO: 1, more preferably at least 90% sequence identity to the polypeptide of SEQ ID NO: 1, most preferably at least 95% sequence identity to the polypeptide of SEQ ID NO: 1; or wherein the functionally active variant of the polypeptide of SEQ ID NO: 2 has at least 80% sequence identity to the parental polypeptide of SEQ ID NO: 2, preferably at least 85% sequence identity to the polypeptide of SEQ ID NO: 2, more preferably at least 90% sequence identity to the polypeptide of SEQ ID NO: 2, most preferably at least 95% sequence identity to the polypeptide of SEQ ID NO: 2. The sequence identity may be determined as detailed above. More preferably, the functionally active variant of the polypeptide of SEQ ID NO: 1 has at least 96% sequence identity to the polypeptide of SEQ ID NO: 1, preferably at least 97% sequence identity to the polypeptide of SEQ ID NO: 1, more preferably at least 98% sequence identity to the polypeptide of SEQ ID NO: 1, most preferably at least 99% sequence identity to the polypeptide of SEQ ID NO: 1; or wherein the functionally active variant of the polypeptide of SEQ ID NO: 2 has at least 96% sequence identity to the parental polypeptide of SEQ ID NO: 2, preferably at least 97% sequence identity to the polypeptide of SEQ ID NO: 2, more preferably at least 98% sequence identity to the polypeptide of SEQ ID NO: 2, most preferably at least 99% sequence identity to the polypeptide of SEQ ID NO: 2.

As well-known in the art, enzymes may be mutated without significantly impairing their enzymatic activity. Particularly, small additions, deletions or substitutions, especially conservative substitutions, are usually uncritical with respect to enzymatic activity. This applies particularly to C and/or N terminal mutations or mutations outside the catalytic and binding sites. Accordingly, those proteins are subject of the present invention. The above and below definitions of the technical terms apply also to this aspect of the invention.

In another aspect, the present invention relates to a nucleic acid coding for the protein as defined in the previous aspect of the present invention.

The term "nucleic acid" as used herein generally relates to any nucleotide molecule which encodes the protein as defined in the previous aspect of the present invention and which may be of variable length. Examples of a nucleic acid of the invention include, but are not limited to, plasmids, vectors, or any kind of DNA and/or RNA fragment(s) which can be isolated by standard molecular biology procedures, including, e.g. ion-exchange chromatography. A nucleic acid of the invention may be used for transfection or transduction of a particular cell or organism, such as a host cell of the present invention.

Nucleic acid molecule of the present invention may be in the form of RNA, such as mRNA, cRNA or LNA (locked nucleic acid), or in the form of DNA, including, for instance, cDNA and genomic DNA e.g. obtained by cloning or produced by chemical synthetic techniques or by a combination thereof. The DNA may be triple-stranded, double-stranded or single-stranded. Single-stranded DNA may be the coding strand, also known as the sense strand, or it may be the non-coding strand, also referred to as the anti-sense strand. Nucleic acid molecule as used herein also refers to, among other, single- and double-stranded DNA, DNA that is a mixture of single- and double-stranded RNA, and RNA that is a mixture of single- and double-stranded regions, hybrid molecules comprising DNA and RNA that may be single-stranded or, more typically, double-stranded, or triple-stranded, or a mixture of single- and double-stranded regions. In addition, nucleic acid molecule as used herein refers to triple-stranded regions comprising RNA or DNA or both RNA and DNA.

Additionally, the nucleic acid may contain one or more modified bases. Such nucleic acids may also contain modifications e.g. in the ribose-phosphate backbone to increase stability and half life of such molecules in physiological environments. Thus, DNAs or RNAs with backbones modified for stability or for other reasons are "nucleic acid molecule" as that feature is intended herein. Moreover, DNAs or RNAs comprising unusual bases, such as inosine, or modified bases, such as tritylated bases, to name just two examples, are nucleic acid molecule within the context of the present invention. It will be appreciated that a great variety of modifications have been made to DNA and RNA that serve many useful purposes known to those of skill in the art. The term nucleic acid molecule as it is employed herein embraces such chemically, enzymatically or metabolically modified forms of nucleic acid molecule, as well as the chemical forms of DNA and RNA characteristic of viruses and cells, including simple and complex cells, inter alia.

Furthermore, the nucleic acid molecule encoding the protein as defined in the previous aspect of the present invention can be functionally linked, using standard techniques such as standard cloning techniques, to any desired sequence, such as a regulatory sequence, leader sequence, heterologous marker sequence or a heterologous coding sequence to create a fusion protein.

The nucleic acid of the invention may be originally formed in vitro or in a cell in culture, in general, by the manipulation of nucleic acids by endonucleases and/or exonucleases and/or polymerases and/or ligases and/or recombinases or other methods known to the skilled practitioner to produce the nucleic acids.

The nucleic acid of the invention may be comprised in a vector, such as an expression vector, wherein the nucleic acid is operably linked to a promoter sequence capable of promoting the expression of the nucleic acid in a host cell.

Accordingly, in another aspect, the present invention relates to a vector comprising the nucleic acid as defined in the previous aspect of the present invention or a nucleic acid encoding the protein as defined above in the context of the present invention.

As used herein, the term "expression vector" or "vector" generally refers to any kind of nucleic acid molecule that can be used to express a protein of interest in a cell (see also above details on the nucleic acids of the present invention). In particular, the vector of the invention can be any plasmid or vector known to the person skilled in the art which is suitable for expressing a protein in a particular host cell including, but not limited to, mammalian cells, bacterial cell, and yeast cells. An expression construct of the present invention may also be a nucleic acid which encodes the protein of the invention, and which is used for subsequent cloning into a respective vector to ensure expression. Plasmids and vectors for protein expression are well known in the art, and can be commercially purchased from diverse suppliers including, e.g., Promega (Madison, Wis., USA), Qiagen (Hilden, Germany), Invitrogen (Carlsbad, Calif., USA), or MoBiTec (Germany) Methods of protein expression are well known to the person skilled in the art and are, e.g., described in Sambrook et al., 2000 (Molecular Cloning: A laboratory manual, Third Edition).

The vector may additionally include nucleic acid sequences that permit it to replicate in the host cell, such as an origin of replication, one or more therapeutic genes and/or selectable marker genes and other genetic elements known in the art such as regulatory elements directing transcription, translation and/or secretion of the encoded protein. The vector may be used to transduce, transform or infect a cell, thereby causing the cell to express nucleic acids and/or proteins other than those native to the cell. The vector optionally includes materials to aid in achieving entry of the nucleic acid into the cell, such as a viral particle, liposome, protein coating or the like. Numerous types of appropriate expression vectors are known in the art for protein expression, by standard molecular biology techniques. Such vectors are selected from among conventional vector types including insects, e.g., baculovirus expression, or yeast, fungal, bacterial or viral expression systems. Other appropriate expression vectors, of which numerous types are known in the art, can also be used for this purpose. Methods for obtaining such expression vectors are well-known (see, e.g. Sambrook et al, supra).

As detailed above, the nucleic acid which encodes a protein of the invention is operably linked to sequence which is suitable for driving the expression of a protein in a host cell, in order to ensure expression of the protein. However, it is encompassed within the present invention that the claimed expression construct may represent an intermediate product, which is subsequently cloned into a suitable expression vector to ensure expression of the protein. The expression vector of the present invention may further comprise all kind of nucleic acid sequences, including, but not limited to, polyadenylation signals, splice donor and splice acceptor signals, intervening sequences, transcriptional enhancer sequences, translational enhancer sequences, drug resistance gene(s) or alike. Optionally, the drug resistance gene may be operably linked to an internal ribosome entry site (IRES), which might be either cell cycle-specific or cell cycle-independent.

The term "operably linked" as used herein generally means that the gene elements are arranged as such that they function in concert for their intended purposes, e.g. in that transcription is initiated by the promoter and proceeds through the DNA sequence encoding the protein of the present invention. That is, RNA polymerase transcribes the sequence encoding the fusion protein into mRNA, which in then spliced and translated into a protein.

The term "promoter sequence" as used in the context of the present invention generally refers to any kind of regulatory DNA sequence operably linked to a downstream coding sequence, wherein said promoter is capable of binding RNA polymerase and initiating transcription of the encoded open reading frame in a cell, thereby driving the expression of said downstream coding sequence. The promoter sequence of the present invention can be any kind of promoter sequence known to the person skilled in the art, including, but not limited to, constitutive promoters, inducible promoters, cell cycle-specific promoters, and cell type-specific promoters.

Unless defined otherwise, all technical and scientific terms and any acronyms used herein have the same meanings as commonly understood by one of ordinary skill in the art in the field of the invention. Definitions of common terms in molecular biology can be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

EXAMPLES

Methods
Reaction Setup:

Preparative scale biotransformations using *E. coli* BL21 (DE3) whole cells with overexpressed different proline hydroxylases (PHs) as a biocatalyst were performed in a total volume of 30 mL. Unless stated otherwise, reactions using PHs were performed at 15° C. (using a cryostat) in a 100 mL flask with mechanical stirrer, including pH- and temperature sensor. Reactions were performed at pH 7.0, which was kept constant using 1-2 M HCl-solution and a titration system from Metrohm (Titrando 902, Touch control). Concentrations, listed in the following reaction description are related to the starting volume (30 mL).

L-Pipecolic acid (PA) (1) (25 mM-150 mM) was dissolved in buffer containing *E. coli* BL21(DE3) whole cells expressing PH (83 g/L wet cell mass). α-Ketoglutaric acid disodium salt (αKG) (2 eq.), sodium ascorbate (0.03 eq.), Mohr's salt (0.01 eq.) and antifoam Y-30 (2% v/v) were added from stock solutions prepared in buffer. Reactions were stirred and a constant flow of water saturated air was applied (250 mL/min).

The pH was kept constant by addition of a 1-2 M HCl.

After different reaction times samples were taken and analyzed by HPLC after dansylchloride derivatization. Diastereomeric excess was analyzed by HPLC, after Fluorenylmethoxycarbonyl chloride (FMOC) derivatization. Derivatization and HPLC methods are described below.

Dansylchloride Derivatization:

100 μL of the reaction mixture were taken from the reaction and centrifuged for 10 min at 14,100×g. 20 μL (5 mM final concentration, 258 μg, 2 μmol) of the supernatant were transferred into a new microreaction tube and 220 μL (22 μmol) of a 1 M NaHCO$_3$ solution was added. Afterwards 160 μL of a 6 g/L dansylchloride solution in acetonitrile was added and the reaction solution was shaken in an Eppendorf ThermoMixer at 55° C. and 850 rpm for 15 min. The reaction solution was centrifuged at 14,100×g for 5 min 50 μL of the supernatant was used for conversion determination using HPLC.

Conversion Determination Using HPLC-Analysis after Dansylchloride Derivatization

| Method: | flow: | 1 mL/min |
|---|---|---|
| | Column temperature: | 40° C. |
| | Stationary phase: | Waters Xbridge C18 (2.5 μm, 2.1 × 50 mm) |
| | Mobile phase: | A: H$_2$O + 0.1% TFA; B: ACN + 0.1% TFA |

| Time [min] | A [%] | B [%] | Remarks |
|---|---|---|---|
| 0 | 90 | 10 | — |
| 3 | 70 | 30 | linear gradient |
| 3.2 | 0 | 100 | linear gradient |
| 4 | 0 | 100 | — |
| 4.1 | 90 | 10 | linear gradient |
| 5 | 90 | 10 | — |

Diastereometric Excess Determination Via HPLC-Analysis after Fmoc Derivatization:

| Method: | flow: | 2 mL/min |
|---|---|---|
| | Column temperature: | 30° C. |
| | Stationary phase: | Waters Xbridge C18 (2.5 μm, 2.1 × 50 mm) |
| | Mobile phase: | A: H$_2$O + 0.02% formic acid; B: ACN + 0.02% formic acid; Diluent: ACN |

| Time [min] | A [%] | B [%] | Remarks |
|---|---|---|---|
| 0 | 70 | 30 | — |
| 0.25 | 70 | 30 | — |
| 2.25 | 0 | 100 | linear gradient |
| 4 | 0 | 100 | — |
| 5.5 | 70 | 30 | Re-equilibration |

Derivatization:

For sample derivatization an in-line derivatization program was set up, as known to the person skilled in the art. The following reagents were used for the derivatization procedure: 1) Borate buffer 0.4 M (pH 10.2; from Agilent; Art. No. 5061-3339), 2) Acetonitrile, 3) FMOC chloride solution (50 mg/mL in Acetonitrile). 2 volumes of Reagent 1) were mixed with 0.25 volumes of the sample and 0.5 volumes of 3) were added. The resulting derivatization mixture was mixed and left to react for 0.1 min prior to injection. After injection the injection needle was washed with 10 μL Acetonitrile.

Example 1 Comparison of Different Newly Identified Proline Hydroxylases

For the identification of new proline hydroxylases, 46 genes were selected. The corresponding proteins were selected for further analysis and tested for there hydroxylase activity. Eighteen of the proteins did show hydroxylase activity for L-PA and three of them did show predominant formation of the 5-HPA regio-isomer.

The three remaining enzymes showed hydroxylase activity and good regio-selectivity. They were screened for stereo-selectivity under the following conditions (0.5 ml) that have previously been determined as suitable for the corresponding enzymes:

PH from *Micromonospora echinospora* (referred to as PH05): 10 mM PA, 20 mM αKG, 1.5 mM Ascorbic acid (sodium salt), 0.5 mM Mohr's salt, 25% (v/v) lysate, pH 5.5, 5° C.

PH from *Micromonospora chokoriensis* (referred to as PH11): 10 mM PA, 20 mM αKG, 1.5 mM Ascorbic acid (sodium salt), 0.5 mM Mohr's salt, 90% (v/v) lysate, pH 6.0, 25° C.

PH from *Kordia jejudonensis* (referred to as PH12): 10 mM PA, 20 mM αKG, 1.5 mM Ascorbic acid (sodium salt), 0.5 mM Mohr's salt, 25% (v/v) lysate, pH 6.0, 25° C.

Cell lysates were prepared by re-suspending 1 g of wet cell paste in 2 mL potassium phosphate buffer (50 mM, pH 7). Cells were lysed by ultrasonication as known to the person skilled in the art. Cell debris was removed prior to the reaction by centrifugation. The reaction conditions for the enzymes were determined prior to the detailed characterization (results not shown).

The results of the screening may be summarized as follows:

TABLE 1

Results of the screening of proline hydroxylases

| PH | Regio-Selectivity | Stereo-Selectivity | Conversion/% |
|---|---|---|---|
| 5 | 5-HPA | >99% de | 82% |
| 11 | 5-HPA | >85.5% de | 95% |
| 12 | 5-HPA (1% 3-HPA) | >99% de | 79% |

Two proline hydroxylases (PH05 and PH 12) were found to be of particular interest, as they were characterized by sufficient pipecolic acid hydroxylase activity and regio-selectivity for 5-HPA as well as stereo-selectivity for (S,S)-cis-5-HPA (cis-5-HPA) 2.

The proline hydroxylase PH 05 relates to SEQ ID NO: 1 and the proline hydroxylase PH 12 relates to SEQ ID NO: 2.

Example 2 Detailed Description of Preparative Scale Biotransformation with Proline Hydroxylase PH05

In view of the fact that proline hydroxylases PH05 and PH12 were characterized by pipecolic acid hydroxylase activity and intended regio-selectivity, they were further characterized:

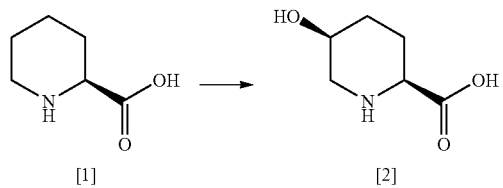 [SMILES: O=C(O)[C@@H]1CCCCN1 ; O=C(O)[C@@H]1CC[C@H](O)CN1]

The preparative scale biotransformation of PA 1 to cis-5-HPA 2 was performed using *E. coli* whole cells with overexpressed proline hydroxylases (PH) from *Micromonospora echinospora* (PH05) as a biocatalyst. This reaction was performed on 4.5 mmol PA (1) scale (580.5 mg, ~19 g/L) at 15° C. and 83.3 g/L whole cells in 30 mL volume, using a substrate feeding approach and a Metrohm pH Stat.

L-Pipecolic acid (PA) (1) (0.387 g, 3 mmol, 100 mM) was dissolved in 30 mL potassium phosphate buffer (100 mM, pH 7) containing *E. coli* BL21(DE3) whole cells expressing PH05 (83 g/L wet cell mass), α-Ketoglutaric acid disodium salt (αKG) (1.356 g, 6 mmol, 200 mM, 2 eq.), sodium ascorbate (0.018 g, 0.09 mmol, 3 mM, 0.03 eq.) and Mohr's salt (0.012 g, 0.03 mmol, 1 mM, 0.01 eq.). 600 µL (2% v/v) antifoam Y-30 was added. Reactions were stirred at 15° C. and a constant flow of water saturated air was applied (250 ml/min).

PA 1 (195 mg, 1.5 mmol, 50 mM) and αKG were fed to the reaction (as depicted in FIG. 1A, PA at 68.5 h and αKG after the following timepoints: 50 h (340 mg, 1.5 mmol, 50 mM), 68.5 h (677 mg, 3 mmol, 100 mM), 75 h (170 mg, 0.75 mmol, 25 mM).

The pH was kept constant by addition of a 1 M HCl solution consuming 30 mL (set as the limit) (30 mmol) during 89 h.

Figure 2A:
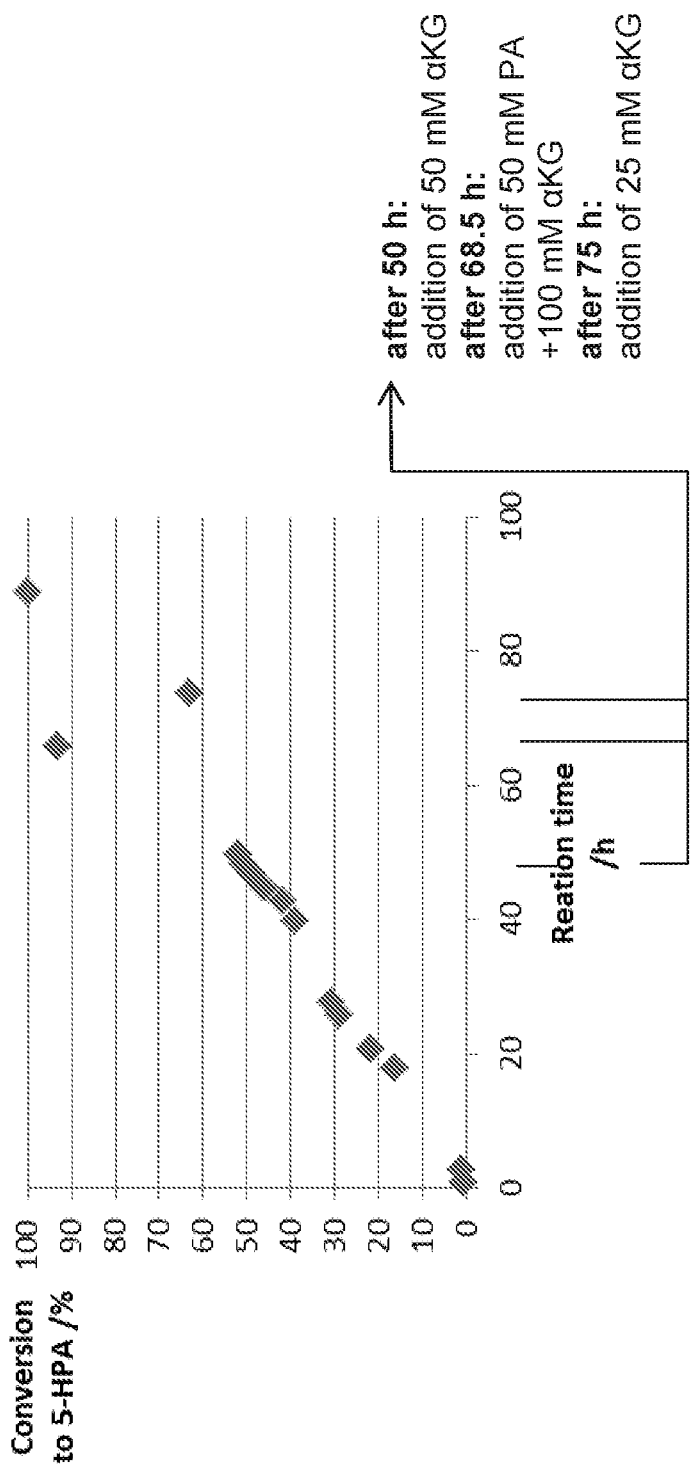
FIGS. 2A-2C illustrate exemplary preparative scale biotransformation using *E. coli* BL21(DE3) whole cells with overexpressed proline hydroxylase PH05.

Previously performed reaction parameter determinations on small scale (~6.5 mg/mL) have shown that the high conversions for PH05-catalyzed reactions using whole cells could be obtained for reactions performed at 15° C. with air intake. It was also found that additional feeding of αKG was necessary to reach high conversions. To monitor the reaction progress after different reaction times samples were taken at different time points (1 h, 3 h, 18 h, 21 h, . . . , 89 h) (FIG. 2 A). Conversion of PA 1 to 5-HPA 2 was monitored by HPLC (see FIG. 2 B).

Figure 2B:
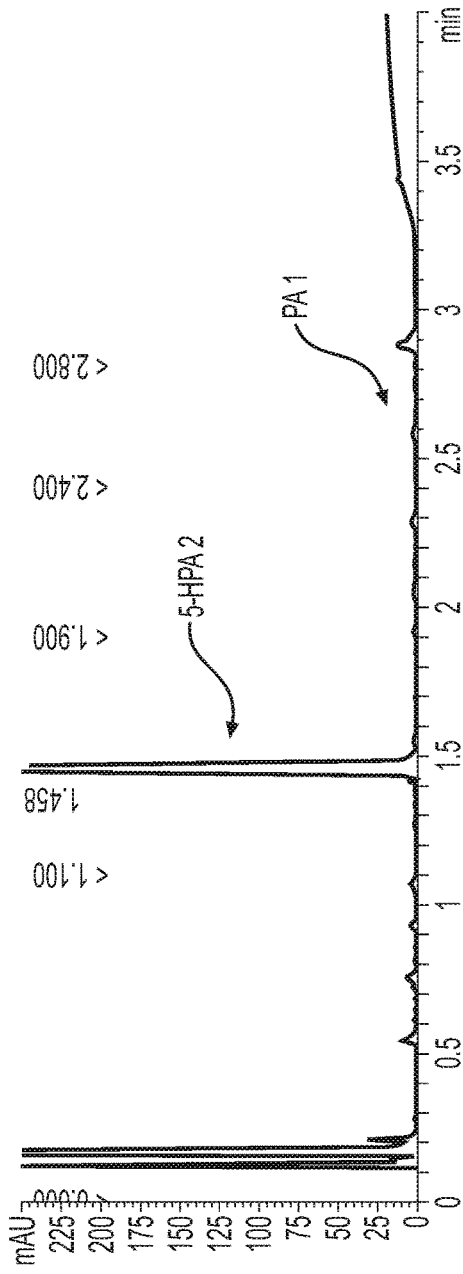
Figure 2C:
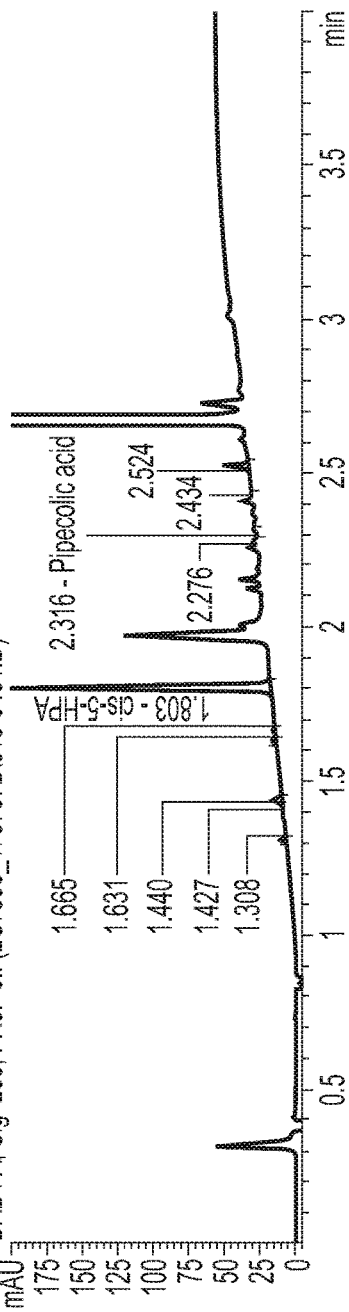

After 68.5 h 93% of PA 1 (3 mmol) was converted to cis-5-HPA 2. Additional 1.5 mmol PA 1 (0.5× initial amount) and 3 mmol αKG (2 eq.) were added to the reaction mixture. A conversion of L-PA 1 to (S,S)-cis-5-HPA 2 of >98% was detected after a total reaction time of 89 h. In FIG. 2B, the HPLC-chromatogram of the reaction mixture after 89 h reaction time is shown. Dansylchloride derivatization was performed beforehand. In the chromatogram of the 89 h sample only a trace signal for the substrate PA 1 is left ($t_r$~2.55 min). The signal at $t_r$~1.45 min is related to the desired product 5-HPA 2.

Diastereomeric excess of the product was determined using HPLC as well with inline Fluorenylmethyloxycarbonyl chloride (Fmoc) derivatization. In FIG. 1C the HPLC-chromatogram of the 89 h sample after cell removal and inline-Fmoc derivatization is shown. No trans-5-HPA 3 could be detected. The signal for the trans-5-HPA 3 diastereomer is expected at a retention time of $t_r$~1.7 min, but only the signal of 5-cis-HPA 2 at $t_r$~1.8 min is visible. Using this HPLC-method ~1% residual PA 1 was detected. As visible in FIG. 2C there are many background signals in the HPLC-chromatograms using inline-Fmoc derivatization, which are related to the Fmoc derivatization.

To conclude this experiment, 4.5 mmol (580.5 mg) PA 1 in 30 mL reaction volume (~19 g/L) using 83.33 g/L (OD600~50) whole cell catalyst including PH05 was converted to 5-cis-HPA 2 (>98%) without detection of a byproduct.

Example 3 Detailed Description of Preparative Scale Biotransformation with Proline Hydroxylase PH05

L-Pipecolic acid (PA) (1) (0.387 g, 3 mmol, 100 mM) was added to 30 mL potassium phosphate buffer (100 mM, pH 7) containing *E. coli* BL21(DE3) whole cells expressing PH05 (83 g/L wet cell mass), α-Ketoglutaric acid disodium salt (αKG) (1.356 g, 6 mmol, 200 mM, 2 eq.), sodium ascorbate (0.018 g, 3 mM, 0.03 eq.) and Mohr's salt (0.012 g, 0.03 mmol, 1 mM, 0.01 eq.). 600 µL (2% v/v) antifoam Y-30 were added and the reaction was stirred at 15° C. while a constant flow of water saturated air was applied (250 mL/min).

Figure 3A:
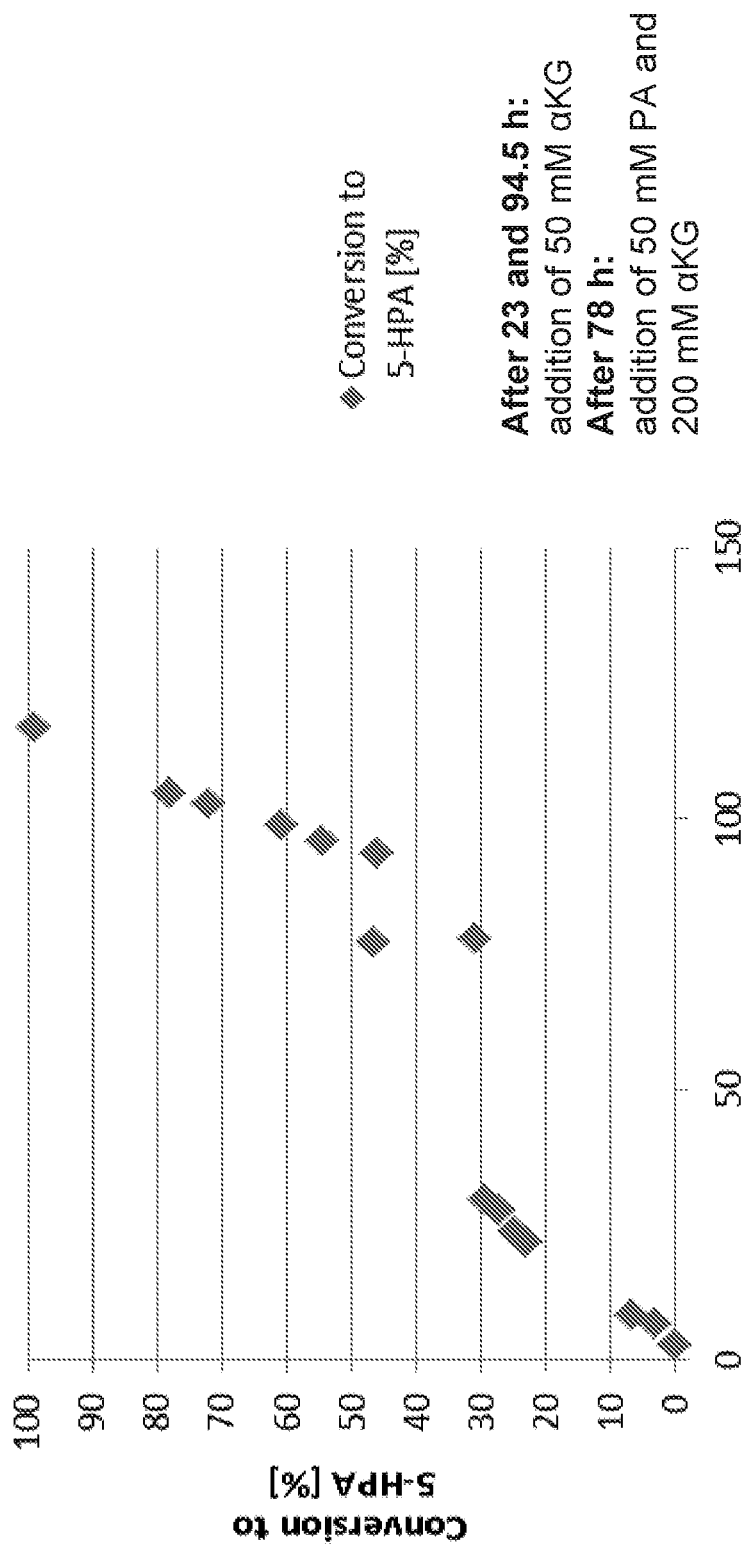

Additional amounts of PA 1 and αKG were fed to the reaction (as depicted in FIG. 3A). PA 1 (195 mg, 1.5 mmol, 50 mM) and αKG (1.356 g, 6 mmol, 200 mM) were added at 78 h and αKG (each 340 mg, ~1.5 mmol, ~50 mM) was added after the following timepoints: 23 and 94.5 h. The pH was kept constant by addition of a 2 M HCl solution (10 mL, 26 mmol) over the reaction time.

After 117 h about 99% conversion of PA 1 to 5-cis-HPA 2 has been detected. The results are shown in FIGS. 3A-3C.

Example 4 Preparative Scale Biotransformation with PH05 at a PA 1 Concentration of ~0.19 g/L and with αKG Additions at 25 mM and 100 mM L-Pipecolic acid (PA) (1) (0.387 g, 3 mmol, 100 mM) was dissolved in 30 mL potassium phosphate buffer (100 mM, pH 7) containing E. coli BL21(DE3) whole cells expressing PH05 (83 g/L wet cell mass), α-Ketoglutaric acid disodium salt (αKG) (1.356 g, 6 mmol, 200 mM, 2 eq.), sodium ascorbate (0.018 g, 0.09 mmol, 3 mM, 0.03 eq.) and Mohr's salt (0.012 g, 0.03 mmol, 1 mM, 0.01 eq.). 600 μL (2% v/v) antifoam Y-30 were added and reactions were stirred at 15° C. while a constant flow of water saturated air was applied (250 mL/min).

Figure 4A:
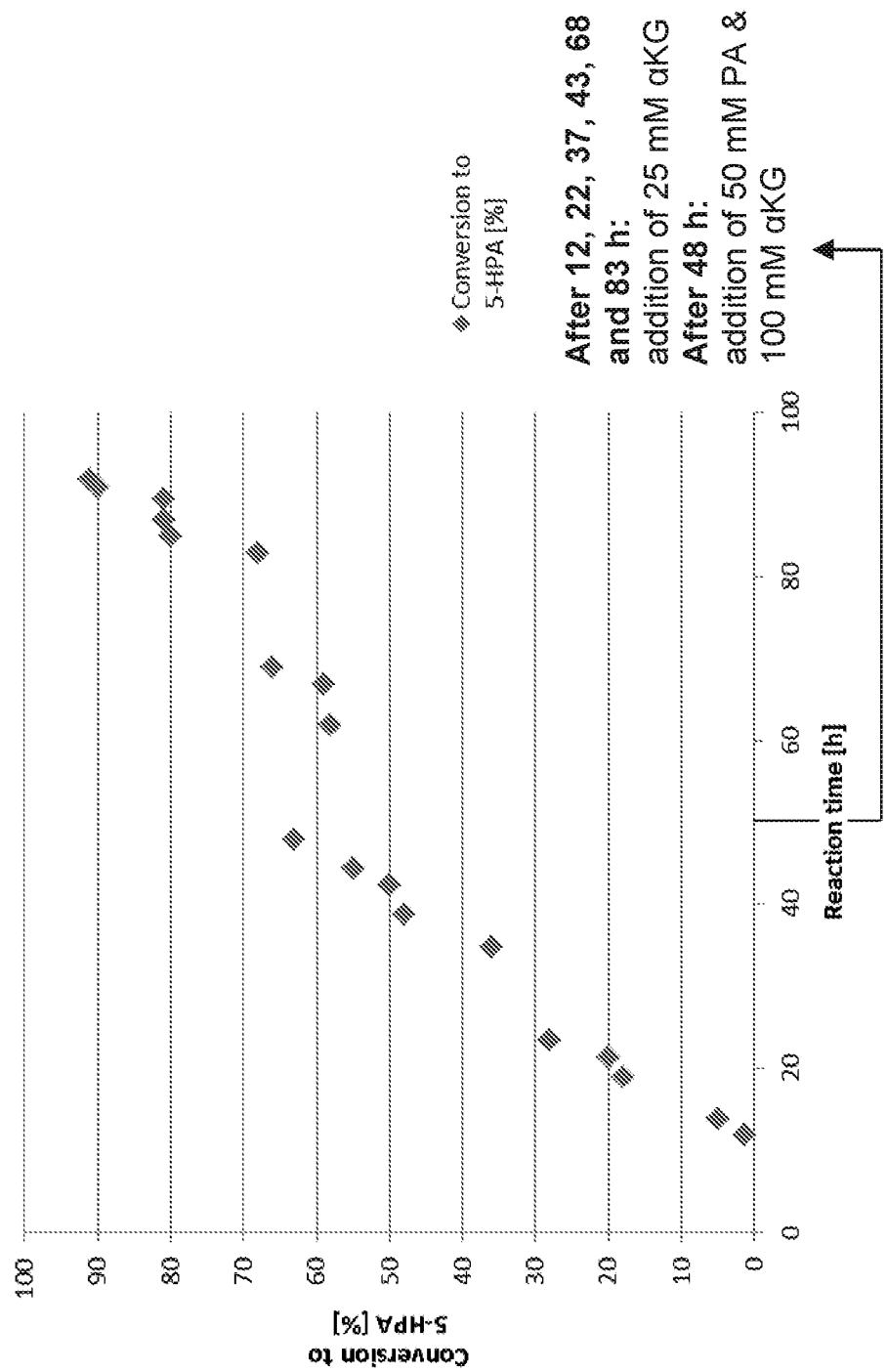
FIGS. 4A-4C illustrate preparative scale biotransformation using proline hydroxylase PH05 at various conditions.

Additional amounts of PA 1 and αKG were fed to the reaction (as depicted in FIG. 4A). PA 1 (195 mg, 1.5 mmol, 50 mM) and αKG (0.678 g, 3 mmol, 2 eq., 100 mM) were added at 48 h and αKG (each 170 mg, 0.75 mmol, 25 mM) was added after the following time points: 12, 22, 37, 43, 68, 83 h. The pH was kept constant by addition of a 2 M HCl solution (13 mL, 26 mmol) over the reaction time.

Figure 4B:
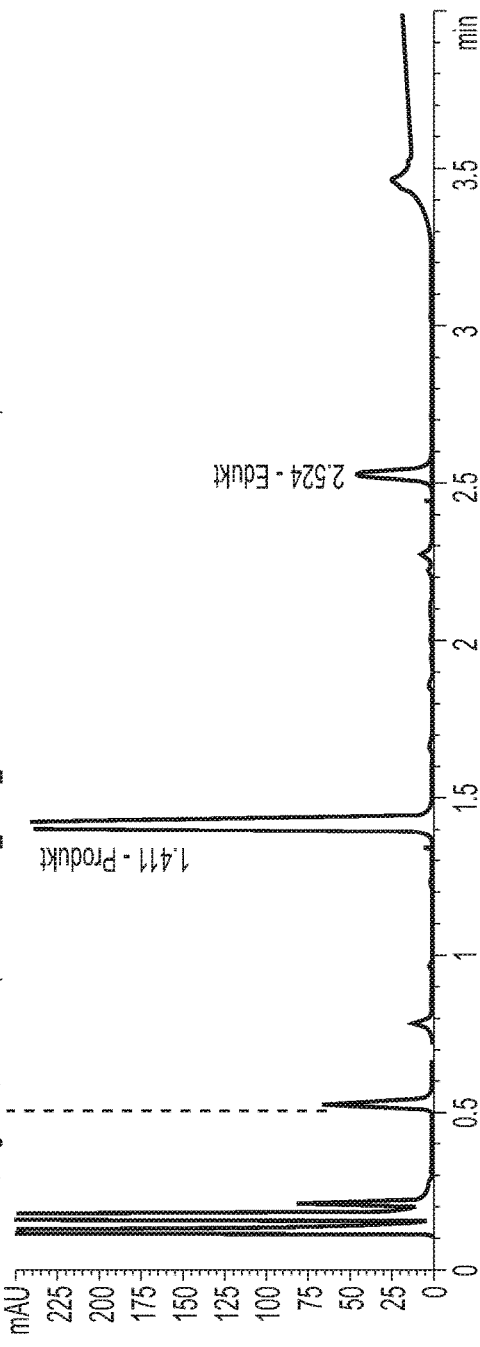
Figure 4C:
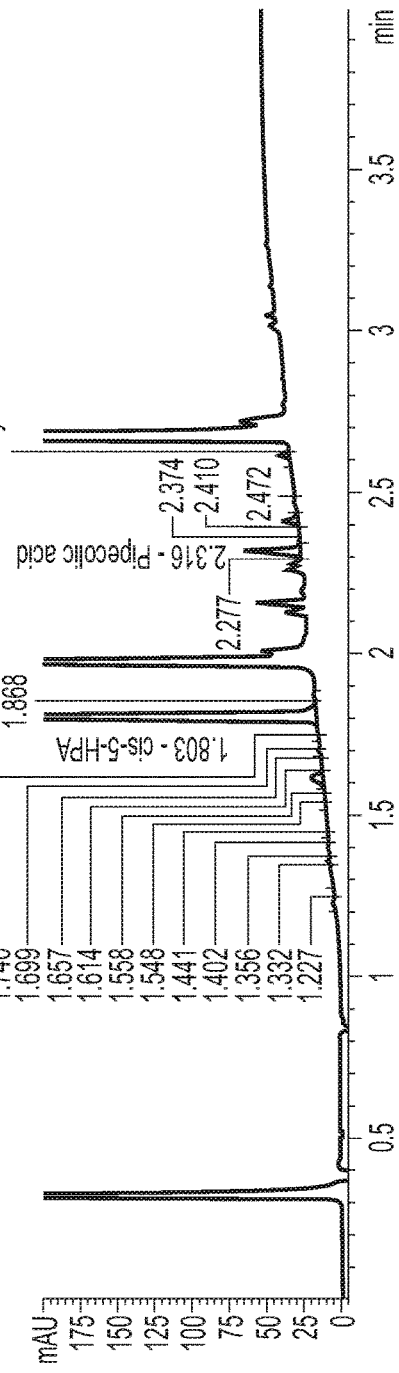

After 92 h, 91% conversion of PA 1 to cis-5-HPA 2 was detected. The results are shown in FIGS. 4A-4C.

Example 5 Preparative Scale Biotransformation with PH05 at a PA 1 Concentration of ~0.3.2 g/L L-Pipecolic acid (PA) (1) (~0.1 g, 0.75 mmol, 25 mM) was dissolved in 30 mL potassium phosphate buffer (100 mM, pH 7) containing E. coli BL21(DE3) whole cells expressing PH05 (83 g/L wet cell mass), α-Ketoglutaric acid disodium salt (αKG) (0.338 g, 1.5 mmol, 50 mM, 2 eq.), sodium ascorbate (1.5 mM) and Mohr's salt (0.5 mM). 600 μL (2% v/v) antifoam Y-30 were added and reactions were stirred at 15° C. while a constant flow of water saturated air was applied (250 mL/min). The pH was kept constant by addition of a 1 M HCl solution (6 mL, 6 mmol) over the reaction time.

Figure 5A:
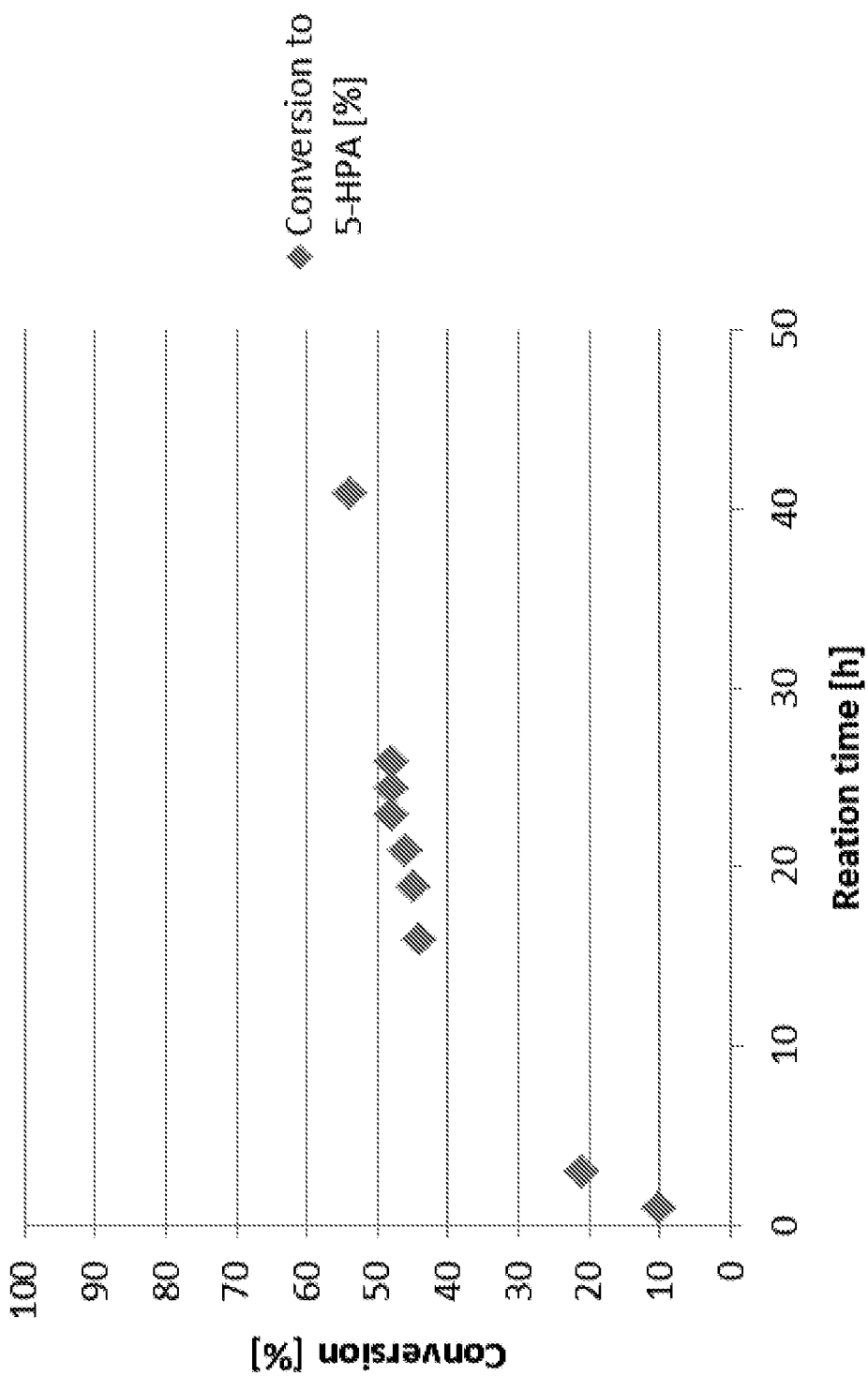

After 41 h, 53% conversion of PA 1 to cis-5-HPA 2 was detected with no further progress in the reaction. The results are shown in FIGS. 5A-5C.

Example 6 Preparative Scale Biotransformation with PH12 at a PA 1 Concentration of 19 g/L

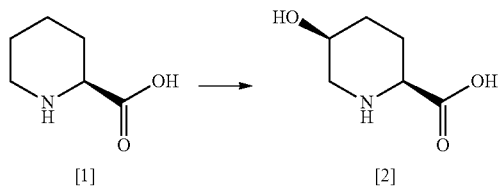

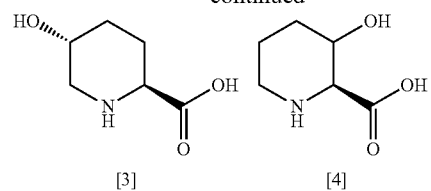

L-Pipecolic acid (PA) (1) (0.194 g, 1.5 mmol, 50 mM) was dissolved in 30 mL potassium phosphate buffer (100 mM, pH 7) containing E. coli BL21(DE3) whole cells expressing PH12 (83 g/L wet cell mass). α-Ketoglutaric acid disodium salt (αKG) (0.678 g, 3 mmol, 2 eq., 100 mM), sodium ascorbate (0.009 g, 0.045 mmol, 1.5 mM, 0.03 eq.), Mohr's salt (0.006 g, 0.015 mmol, 0.5 mM, 0.01 eq.) and 600 μL (2% v/v) antifoam Y-30 was added. Reactions were stirred at 25° C. and a constant flow of water-saturated air was applied (250 mL/min).

Figure 6A:
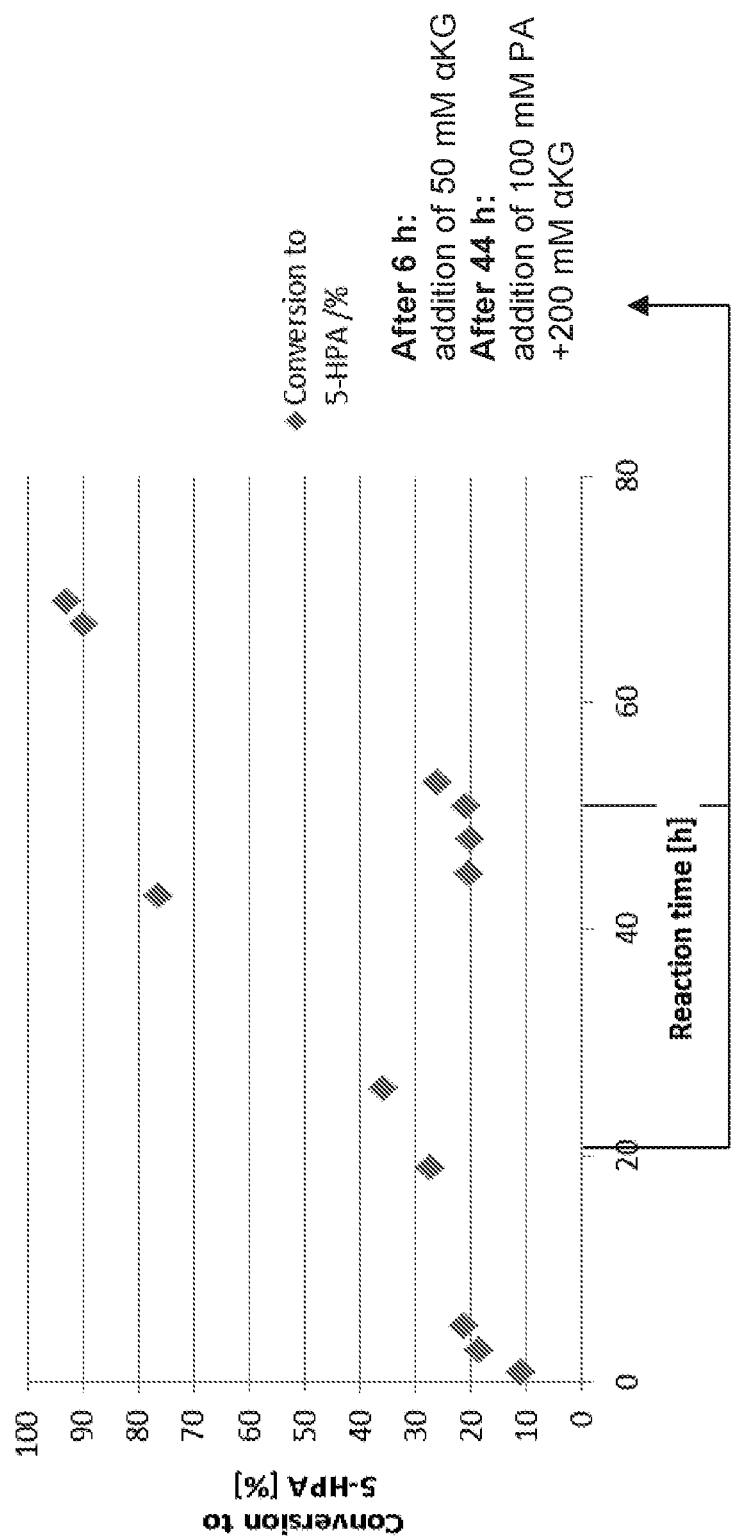
FIGS. 6A-6C illustrate preparative scale biotransformation using proline hydroxylase PH12 at various conditions.

Additional amounts of αKG (340 mg, ~1.5 mmol, ~50 mM) were added after 6 h and L-Pipecolic acid (PA) (1) (387 mg, 3 mmol, 100 mM) and α-Ketoglutaric acid disodium salt (αKG) (1.356 g, 6 mmol, 2 eq., 200 mM) were added after 44 h. Samples were taken after different timepoints as indicated in FIG. 6A. The pH was kept constant by addition of a 1 M HCl solution (30 mL, 30 mmol) over the reaction time.

Figure 6B:
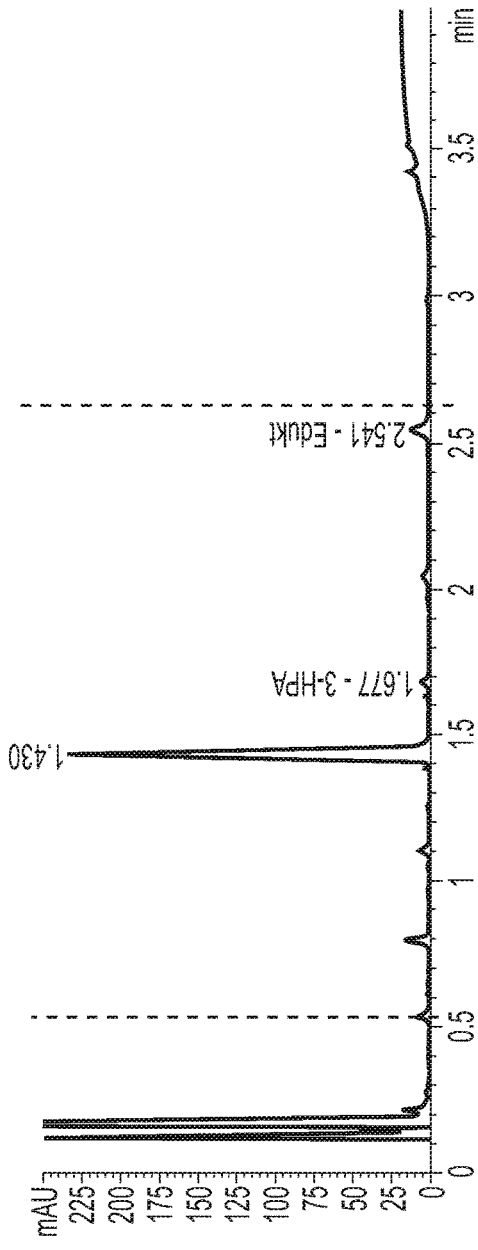
Figure 6C:
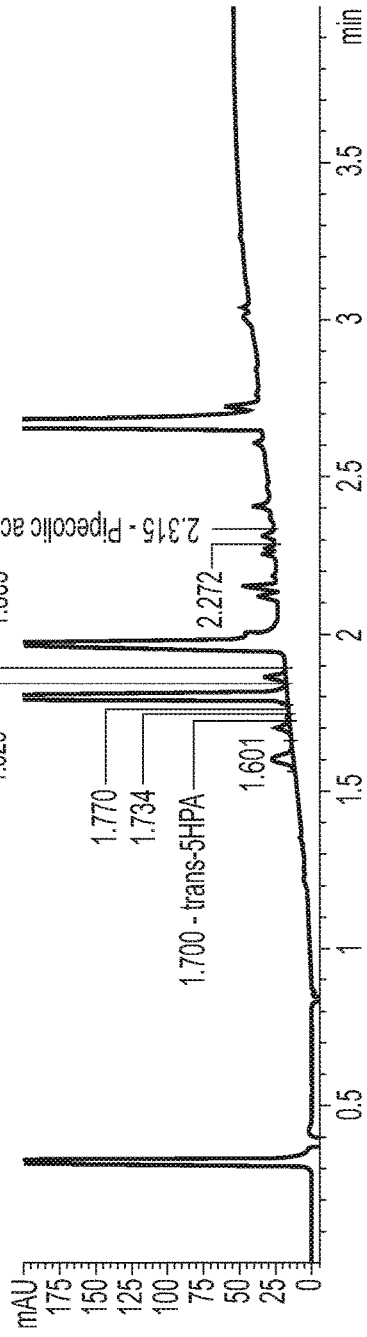

After 68 h, 93% conversion of PA 1 was detected using a total substrate concentration of 150 mM. In contrast to previous experiments with PH05, small amounts (<1%) of 3-HPA 4 and 2.6% (2S,5R)-trans-5-HPA 3 were detected (see FIGS. 6A-6C).

Figure 7A:
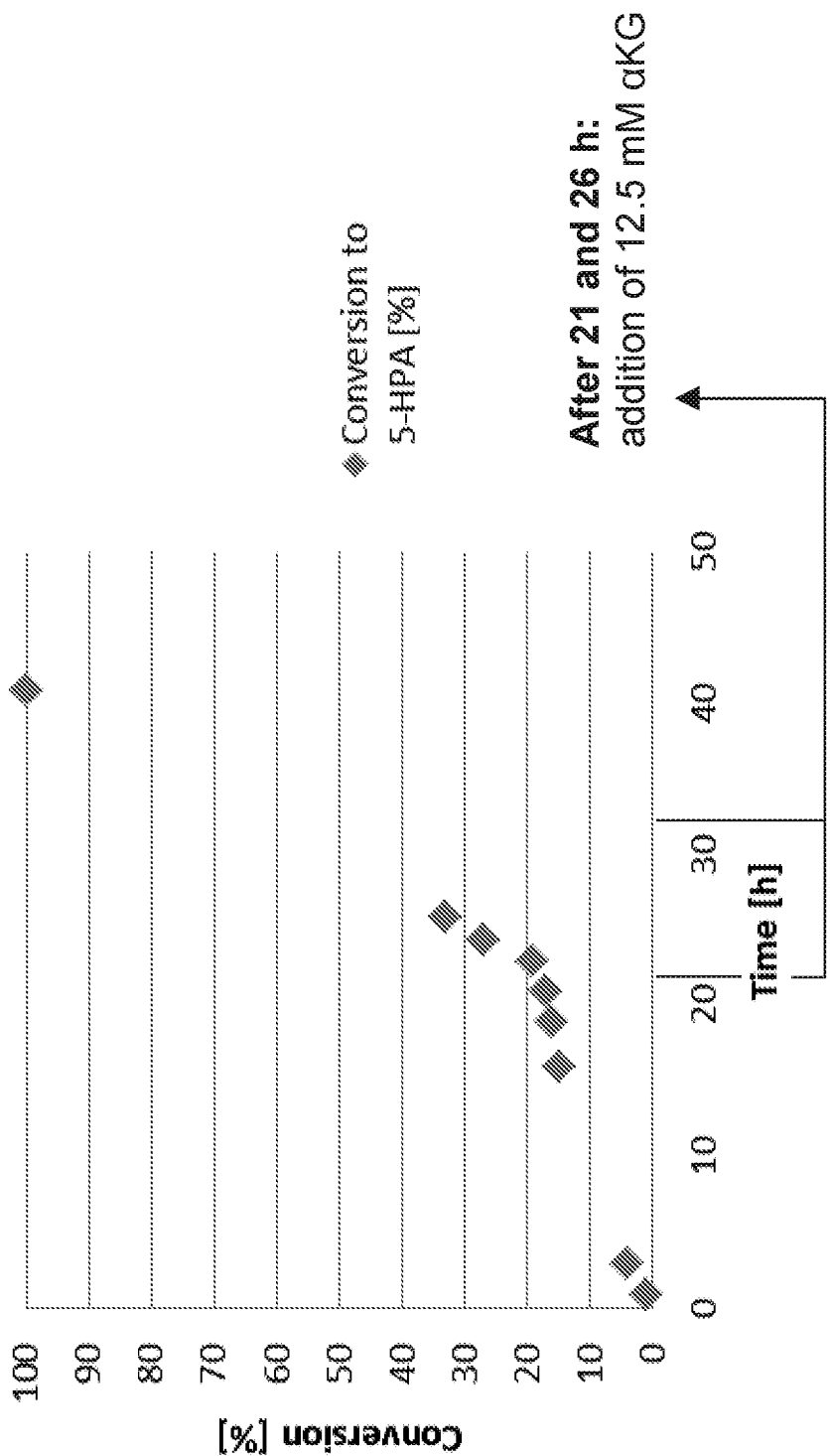

Example 7 Preparative Scale Biotransformation with PH12 at a PA 1 Concentration of 3.2 g/L L-Pipecolic acid (PA) (1) (~0.1 g, 0.75 mmol, 25 mM) was dissolved in 30 mL potassium phosphate buffer (100 mM, pH 7) containing E. coli BL21(DE3) whole cells expressing PH12 (83 g/L wet cell mass). α-Ketoglutaric acid disodium salt (αKG) (0.339 g, 1.5 mmol, 2 eq., 50 mM), sodium ascorbate (1.5 mM), Mohr's salt (0.5 mM). 600 μL (2% v/v) antifoam Y-30 was added. Reactions were stirred at 25° C. and a constant flow of water-saturated air was applied (250 mL/min). The pH was kept constant by addition of a 1 M HCl solution (5 mL, 5 mmol) over the reaction time Additional amounts of α-Ketoglutaric acid disodium salt (αKG) (0.085 g, 0.375 mmol, 0.5 eq., 12.5 mM) were added to the reaction after 21 and 26 h. Samples were taken after the time points indicated in FIG. 7A.

After 41 h, >99% conversion of PA 1 was detected using a total substrate concentration of 25 mM PA 1. In contrast to experiments with PH12 at higher concentrations no 3-HPA 4 and (2S,5R)-trans-5-HPA 3 formation was detected (see FIG. 7).

The examples and embodiments described herein are for illustrative purposes only and in some embodiments, various modifications or changes are to be included within the purview of disclosure and scope of the appended claims.

The invention claimed is:

1. A method of hydroxylating pipecolic acid (PA) or L-pipecolic acid (L-PA), comprising contacting the PA or L-PA with a hydroxylase protein, wherein the protein comprises the amino acid sequence of SEQ ID NO:1 or an amino acid sequence of at least 90% identity to SEQ ID NO:1, wherein the protein has pipecolic acid hydroxylase activity, thereby producing hydroxylated pipecolic acids.

2. The method of claim 1, wherein the protein is the polypeptide of SEQ ID NO: 1.

3. The method of claim 1, wherein the hydroxylated pipecolic acids are hydroxy-pipecolic acid (HPA), 5-hydroxy-pipecolic acid (5-HPA), cis-5-hydroxy-pipecolic acid (cis-5-HPA), or (2S,5S)-cis-5-hydroxy-pipecolic acid ((2S,5S)-cis-5-HPA).

4. The method of claim 3, wherein the protein comprises:
i) a regio selectivity for 5-HPA of at least 90%;
ii) a stereoselectivity for cis-5-HPA of at least 90%; or
iii) a conversion ratio of at least 60%.

5. The method of claim 1, wherein the method takes place in the presence of oxygen.

6. The method of claim 1, wherein the hydroxylation takes place in the presence of an oxygen acceptor/co-substrate and in the presence of $Fe^{2+}$.

7. The method of claim 1, wherein the hydroxylation takes place in an aqueous environment having a pH 4.5 to 8.

8. The method of claim 3, wherein the method further comprises isolating the HPA, the 5-HPA, the cis-5-HPA, or the (2S,5S)-cis-5-HPA.

9. The method of claim 3, wherein the protein comprises:
i) a regio selectivity for 5-HPA of at least 90%;
ii) a stereoselectivity for cis-5-HPA of at least 90%; and
iii) a conversion ratio of at least 60%.

10. The method of claim 1, wherein the protein is produced in a host cell comprising the polypeptide of SEQ ID NO: 1 or a nucleic acid encoding the polypeptide of SEQ ID NO: 1, wherein the cell is not any one of the following: a *Micromonospora echinospora* cell, a *Micromonospora* cell, a Micromonosporaceae cell, a Micromonosporales cell, an Actinobacteria cell, or a bacterial cell.

11. The method of claim 1, wherein the hydroxylation takes place at a temperature of 5° C. to 30° C.

12. The method of claim 1, wherein the hydroxylation takes place at an α-ketoglutarate concentration of from 50 mM to 500 mM with a pipecolic acid (PA) or L-pipecolic acid (L-PA) concentration of from 25 mM to 200 mM.

13. A method of hydroxylating pipecolic acid (PA) or L-pipecolic acid (L-PA) to produce hydroxylated pipecolic acids, comprising contacting the PA or L-PA with the polypeptide of SEQ ID NO:1 in the presence of α-ketoglutarate, wherein the hydroxylated pipecolic acids are HPA, 5-HPA, cis-5-HPA, or (2S,5S)-cis-5-HPA.

\* \* \* \* \*